(12) United States Patent
Huh et al.

(10) Patent No.: US 11,786,406 B2
(45) Date of Patent: Oct. 17, 2023

(54) PROTECTOR FOR WELDING

(71) Applicant: OTOS WING.CO., LTD., Seoul (KR)

(72) Inventors: Moon Young Huh, Seoul (KR); Sung Won Huh, Seoul (KR)

(73) Assignee: OTOS WING.CO., LTD., Seoul (KR)

( * ) Notice: Subject to any disclaimer, the term of this patent is extended or adjusted under 35 U.S.C. 154(b) by 442 days.

(21) Appl. No.: 16/925,669

(22) Filed: Jul. 10, 2020

(65) Prior Publication Data

US 2021/0015672 A1 Jan. 21, 2021

(30) Foreign Application Priority Data

Jul. 16, 2019 (KR) .................... 10-2019-0085827

(51) Int. Cl.
| | | |
|---|---|---|
| *A61F 9/06* | (2006.01) | |
| *B23K 9/32* | (2006.01) | |
| *A62B 17/04* | (2006.01) | |

(52) U.S. Cl.
CPC .............. *A61F 9/064* (2013.01); *B23K 9/322* (2013.01); *A62B 17/04* (2013.01)

(58) Field of Classification Search
CPC . A61F 9/06; A61F 9/064; B23K 9/322; A62B 17/04
See application file for complete search history.

(56) References Cited

U.S. PATENT DOCUMENTS

| | | | | |
|---|---|---|---|---|
| 625,776 A | * | 5/1899 | Von Klein | A42C 5/04 2/175.1 |
| 1,526,322 A | * | 2/1925 | Dehne | A42B 1/201 2/46 |
| 1,663,124 A | * | 3/1928 | Fischer | A42B 1/22 2/175.3 |
| 1,732,357 A | * | 10/1929 | Davis | A61F 9/045 2/12 |
| 2,016,775 A | * | 10/1935 | Gingg | A61F 9/06 2/8.2 |
| 2,103,006 A | * | 12/1937 | Helfenstein | A61F 9/06 2/8.2 |
| D181,737 S | * | 12/1957 | Ligorner | D5/16 |
| 2,817,087 A | * | 12/1957 | Rush | A61F 9/06 2/8.1 |

(Continued)

FOREIGN PATENT DOCUMENTS

| | | |
|---|---|---|
| CN | 2293308 Y | 10/1998 |
| CN | 207168638 U | 4/2018 |

(Continued)

OTHER PUBLICATIONS

Office Action dated May 3, 2021 in related foreign German application No. 102020208049.6, all pgs.

(Continued)

*Primary Examiner* — F Griffin Hall
(74) *Attorney, Agent, or Firm* — KILPATRICK TOWNSEND & STOCKTON LLP

(57) ABSTRACT

Provided is a welding protector which includes a face shield configured to protect a face of a welder and an auxiliary shield disposed adjacent to one edge of the face shield. The auxiliary shield includes a plurality of portions which overlap each other in a first mode and move to reduce an overlapping area when switching from the first mode to a second mode.

18 Claims, 22 Drawing Sheets

(56) References Cited

U.S. PATENT DOCUMENTS

| | | | | |
|---|---|---|---|---|
| 2,837,746 | A | * | 6/1958 | Gundy ................... A42B 1/201<br>2/205 |
| 2,864,092 | A | * | 12/1958 | Hurst ..................... A42B 1/201<br>2/171.03 |
| 3,026,525 | A | * | 3/1962 | Gyorfy ................... A42B 3/322<br>2/202 |
| 3,229,846 | A | * | 1/1966 | Katz ....................... B65F 1/16<br>220/252 |
| 3,514,787 | A | * | 6/1970 | Kennedy, Jr. ........... A42B 3/322<br>D29/104 |
| 3,908,199 | A | * | 9/1975 | Lim ....................... A42B 1/201<br>2/175.1 |
| 3,991,422 | A | * | 11/1976 | Saotome ................ A42B 3/322<br>2/410 |
| 4,057,855 | A | * | 11/1977 | Hovhannessian ...... A42B 1/008<br>2/171.03 |
| 4,091,470 | A | * | 5/1978 | Ryunoshin ............. A42B 3/322<br>2/410 |
| 4,291,417 | A | * | 9/1981 | Pagano .................. A42B 1/201<br>2/202 |
| 4,391,277 | A | * | 7/1983 | Horvat .................. A41C 3/0064<br>450/68 |
| 4,453,276 | A | * | 6/1984 | Smith .................... A42B 1/045<br>2/200.1 |
| 4,508,115 | A | * | 4/1985 | Warncke ................ A62B 17/04<br>128/201.28 |
| 4,556,993 | A | * | 12/1985 | Okamura, Sr. ......... A42B 1/201<br>2/209.12 |
| 4,607,397 | A | * | 8/1986 | Laxo ...................... A42B 3/322<br>2/410 |
| 4,741,053 | A | * | 5/1988 | Okamura, Sr. ......... A42B 1/201<br>2/209.12 |
| 5,628,071 | A | * | 5/1997 | Nezer .................... A42B 3/322<br>2/424 |
| 5,943,716 | A | * | 8/1999 | Chu ....................... A61G 10/04<br>5/423 |
| 5,991,916 | A | * | 11/1999 | Sierra .................... A61F 9/045<br>2/209.12 |
| D425,166 | S | * | 5/2000 | Mattson ........................ D21/837 |
| 6,256,796 | B1 | * | 7/2001 | Fleming ................. A42B 1/24<br>2/244 |
| 6,453,475 | B1 | * | 9/2002 | Johnson ................. A42B 1/201<br>2/209.12 |
| D553,830 | S | * | 10/2007 | Landers ........................ D2/882 |
| 8,128,876 | B2 | * | 3/2012 | Al-Thallab ........ B01D 46/0028<br>422/4 |
| D738,596 | S | * | 9/2015 | Tang ............................. D2/876 |
| D756,612 | S | * | 5/2016 | Broderick ..................... D2/880 |
| D793,359 | S | * | 8/2017 | Katopis ....................... D14/205 |
| 10,226,383 | B2 | * | 3/2019 | Ambring ............ A41D 13/0518 |
| 10,362,816 | B1 | * | 7/2019 | Vigil ..................... A42B 1/206 |
| 11,324,274 | B2 | * | 5/2022 | Nilsson ................. A42B 3/225 |
| 2005/0279396 | A1 | * | 12/2005 | Choi ..................... A45B 11/04<br>135/133 |
| 2006/0143792 | A1 | * | 7/2006 | No ....................... A42B 1/0185<br>2/195.2 |
| 2011/0083251 | A1 | * | 4/2011 | Mandell ............... A42B 1/0188<br>2/209 |

FOREIGN PATENT DOCUMENTS

| | | |
|---|---|---|
| JP | H11-313850 A | 11/1999 |
| KR | 2007-0005491 A | 1/2007 |
| KR | 10-1832801 B1 | 2/2018 |

OTHER PUBLICATIONS

Office Action dated Jul. 28, 2020 in Korean Patent Application No. 10-2019-0085827, filed Jul. 19, 2019, 5 pages. No English translation available.

* cited by examiner

PROTECTOR FOR WELDING

CROSS-REFERENCE TO RELATED APPLICATION

This application claims the benefit of Korean Patent Application No. 10-2019-0085827, filed on Jul. 16, 2019, in the Korean Intellectual Property Office, the disclosure of which is incorporated herein in its entirety by reference.

BACKGROUND

1. Field

One or more embodiments relate to a protector for welding.

2. Description of the Related Art

Protectors are worn to protect a welder from light, high heat, and the like, which are generated during a welding process such as arc welding. Depending on the types of work of the welder, the protectors have various shapes and structures, for example, for covering the eyes of the welder or for covering the head part of the welder.

SUMMARY

A protector may include various components for protecting various parts of the body of a welder, but it is difficult to store the protector including the various components.

The present disclosure is to address several limitations including the aforementioned limitation, and one or more embodiments include a protector for welding (hereinafter, referred to as a welding protector), having excellent storability and portability and capable of protecting at least a portion of the body of a welder. However, this may be merely illustrative, and thus the scope of the present invention is not limited thereby.

Additional aspects will be set forth in part in the description which follows and, in part, will be apparent from the description, or may be learned by practice of the presented embodiments of the disclosure.

According to one or more embodiments, a welding protector includes: a face shield configured to protect a face of a welder; and an auxiliary shield disposed adjacent to one edge of the face shield, wherein the auxiliary shield includes a plurality of portions which overlap each other in a first mode and move to reduce an overlapping area when switching from the first mode to a second mode.

The plurality of portions of the auxiliary shield may be positioned on an inner surface or an outer surface of the face shield in the first mode.

The plurality of portions may include a first portion and a second portion adjacent to each other, wherein the second portion linearly moves to reduce an overlapping area with the first portion when switching from the first mode to the second mode.

The plurality of portions may include a first portion and a second portion adjacent to each other, wherein the second portion rotates around an axis when switching from the first mode to the second mode.

The plurality of portions may include a first portion and a second portion adjacent to each other, wherein the first portion and the second portion are integrally coupled to each other, and the first portion and the second portion are foldable along a folding line between the first portion and the second portion.

The plurality of portions may include a first portion and a second portion adjacent to each other, wherein the second portion linearly moves on the first portion when switching from the first mode to the second mode.

According to one or more embodiments, a welding protector includes: a face shield configured to protect a face of a welder; and an auxiliary shield configured to cover a portion of a head part of the welder and positioned on an inner surface or an outer surface of the face shield, wherein the auxiliary shield includes a hard material, and the auxiliary shield is movable in a direction away from the face shield to increase a covering area of the auxiliary shield configured to cover the portion of the head part.

The auxiliary shield may include a first portion and a second portion adjacent to each other, wherein the second portion is movable to reduce or increase an overlapping area with the first portion.

The second portion may linearly move with respect to the first portion.

One of the first portion and the second portion may include a slide hole that extends in the direction away from the face shield, and the other one includes a protrusion having a central portion disposed in the slide hole.

The second portion may rotate around an axis with respect to the first portion.

The auxiliary shield may include a pair of coupling portions which are coupled to the face shield, and the second portion may rotate with respect to the first portion around an axis that passes though the pair of coupling portions.

The first portion and the second portion may linearly move in one direction with respect to the face shield, and after the linear movement, the second portion may rotate to reduce or increase an overlapping area with the first portion.

Other aspects, features, and advantages will be apparent from the drawings, claims, and description.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
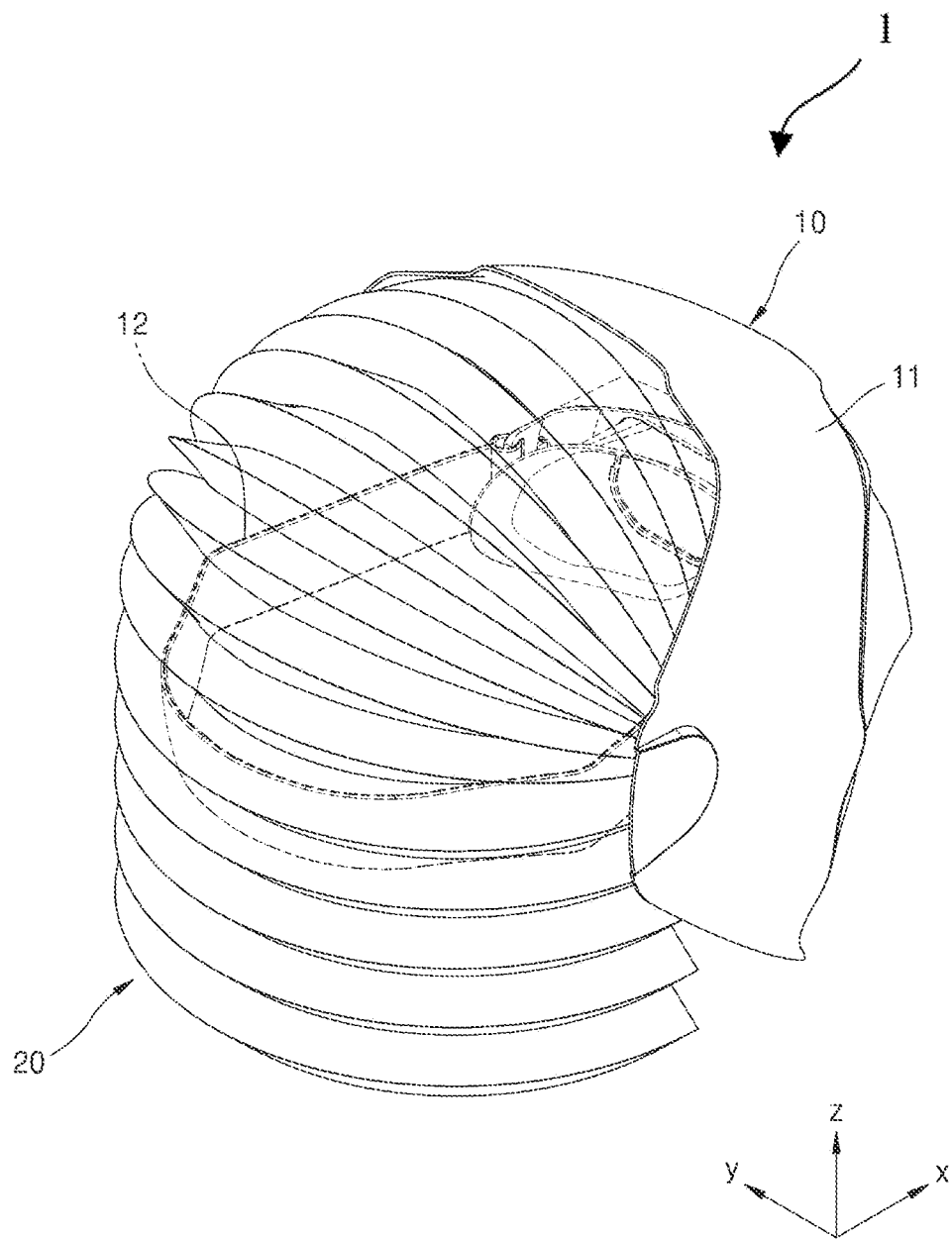
FIG. 1 is a schematic perspective view of a welding protector according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Since the present invention may have diverse modified embodiments, preferred embodiments are illustrated in the drawings and are described in the detailed description of the invention. Effects and features of the present disclosure, and implementation methods thereof will be clarified through following embodiments described in detail with reference to the drawings. The present disclosure may, however, be embodied in various forms and should not be construed as limited to the embodiments set forth herein.

Hereinafter, embodiments of the present disclosure are described in detail with reference to the accompanying drawings, and when describing the present disclosure with reference to the drawings, the identical or corresponding components are given with the same reference numerals, and their duplicated descriptions will be omitted.

In the embodiments, terms "first" and "second" are used to distinguish one component from another component, but these components should not be limited by these terms.

In the embodiments, the singular forms are intended to include the plural forms as well, unless the context clearly indicates otherwise.

In the embodiments, the terms "includes" or "including" when used in this specification are to specify the presence of stated features or components, but do not preclude the addition of one or more other features or components.

In the embodiments, when a portion such as a region or a component is referred to as being "above" or "on" another portion, it can be directly on another portion, or intervening regions or components may also be present therebetween.

In the drawings, the dimensions of elements may be exaggerated or downscaled for clarity. For example, because the size and thickness of each configuration shown in the drawings are arbitrarily shown for ease of description, and the present disclosure is not limited thereto.

When a certain embodiment may be implemented differently, a specific process order may be performed differently from the described order. For example, two consecutively described processes may be performed substantially at the same time or performed in an order opposite to the described order.

In the embodiments, when a region, a component, or the like is referred to as being connected to another region or component, it can be directly connected to the other region or component or be indirectly connected to the other region or component with intervening regions or components interposed therebetween. For example, in the specification when a region, a component, or the like is referred to as being electrically connected to another region or component, it can be directly electrically connected to the other region or component or be indirectly electrically connected to the other region or component with intervening regions or components interposed therebetween.

Figure 2:
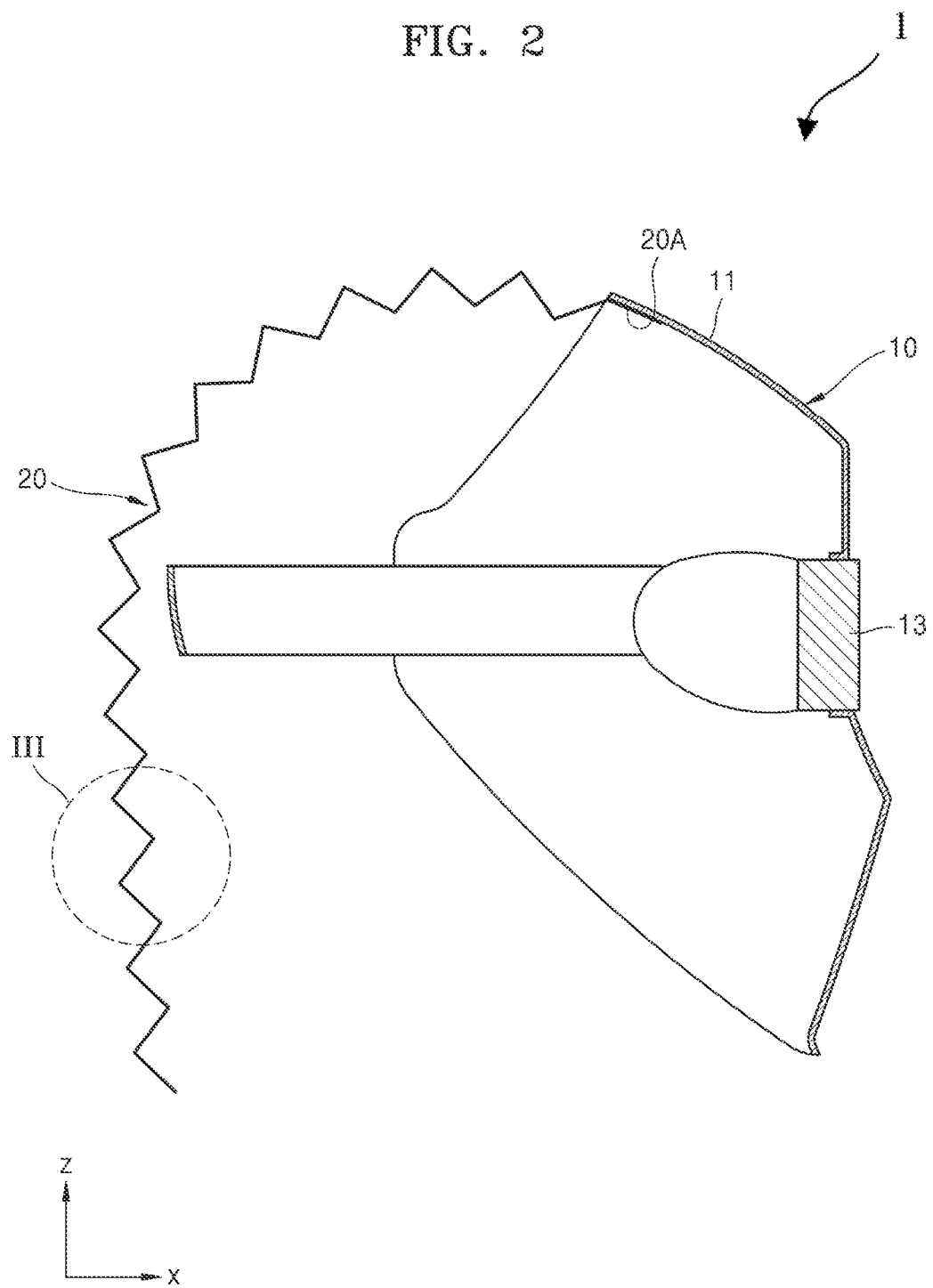
FIG. 2 is a side cross-sectional view of the welding protector.
Figure 3:
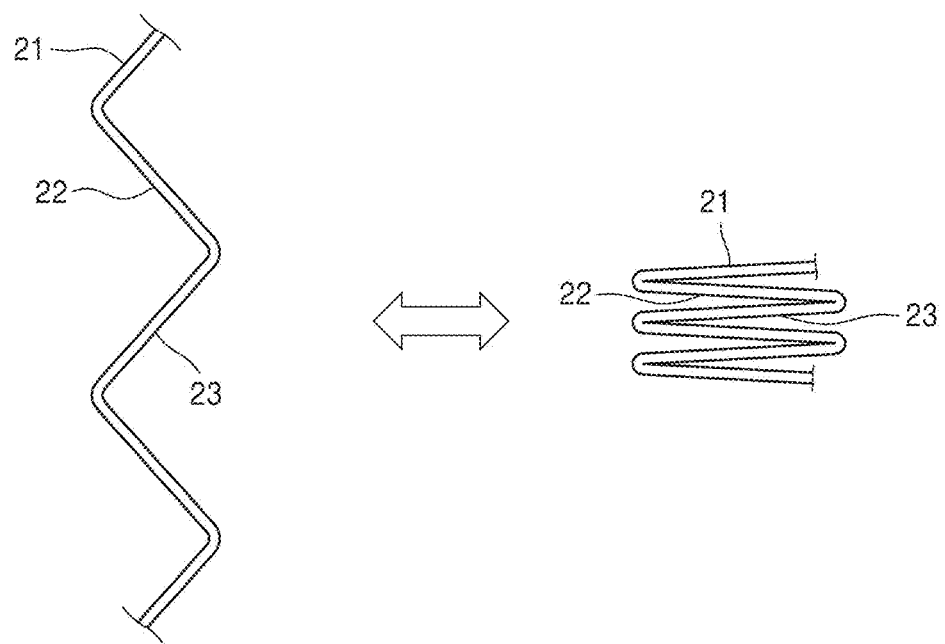
FIG. 3 is a side cross-sectional view showing an overlapping state of an auxiliary shield that corresponds to a region III of FIG. 2.
Figure 4:
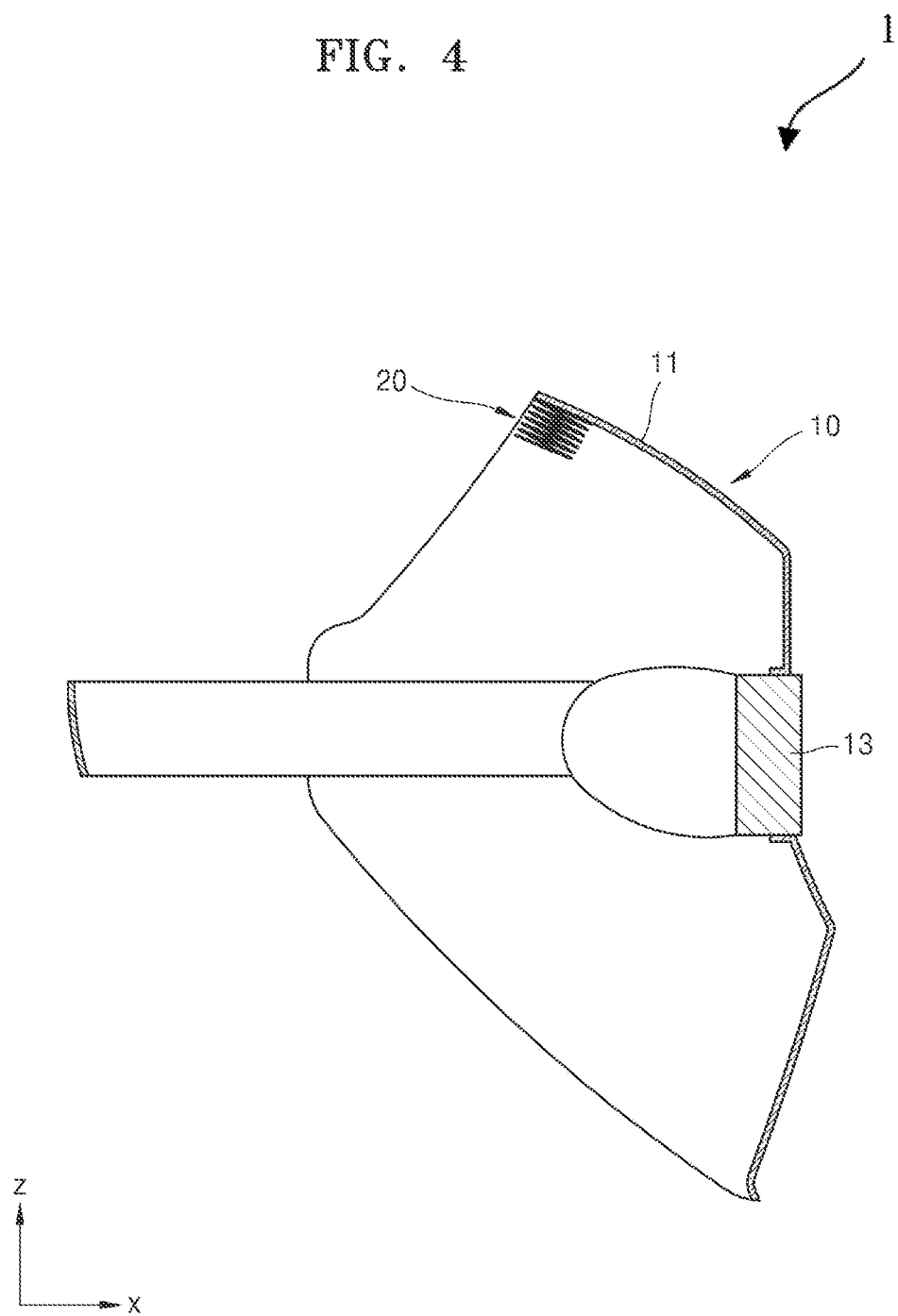
FIG. 4 is a side cross-sectional view of a welding protector according to an embodiment of the present disclosure.

FIG. 1 is a schematic perspective view of a welding protector according to an embodiment of the present disclosure, FIG. 2 is a side cross-sectional view of the welding protector, FIG. 3 is a side cross-sectional view showing an overlapping state of an auxiliary shield that corresponds to a region III of FIG. 2, and FIG. 4 is a side cross-sectional view of a welding protector according to another embodiment.

Referring to FIGS. 1 and 2, a welding protector 1 may include a face shield 10, which protects the face of a welder, and an auxiliary shield 20, which covers other regions of the body of the welder which are not covered by the face shield 10.

The face shield 10 may protect at least a portion of the face of the welder. The face shield 10 may include a main body 11 and a wearing member 12 provided behind the main body 11 and fixing the face shield 10 to the head part of the welder.

The main body 11 may include a hard material having certain strength. The hard material refers to a material capable of maintaining a shape thereof as long as an external force is not applied. The main body 11 may include at least one of metal and plastic. In an embodiment, the main body 11 may include a material resistant to factors such as sparks that may occur during welding and/or an external impact. In an embodiment, the main body 11 may include heat-resistant plastic and/or reinforced plastic.

The wearing member 12 is configured to be in direct contact with the head part of the welder, and one side surface of the wearing member 12, for example, at least a portion of an inner surface that is in direct contact with the head part of the welder, may include a soft material such as a fibrous material and a cushion material.

FIGS. 1 and 2 illustrate that the wearing member 12 includes a band-type strap that is made of a stretchable material and adjustable in length. In another embodiment, the wearing member 12 may include a gear-type rigid strap that is adjustable in length, and a gear may be adjusted to the size of the head part of the welder through relative movements of members constituting the gear.

A light blocking member 13 positioned in a region corresponding to the eyes of the welder may be provided inside the main body 11. In an embodiment, the light blocking member 13 may include an electro-optical element. The electro-optical element may include liquid crystals, and a darkness level of the elements of the light blocking member 13 may be adjusted according to an alignment direction of the liquid crystals of the electro-optical elements. The light blocking member 13 may include an automatic light blocking filter. The automatic light blocking filter may adjust a darkness level on the basis of light sensing information of a sensor provided in the vicinity of the light blocking member 13.

The auxiliary shield 20 may protect the body of the welder which are not covered by the face shield 10, for example, the top of the head part, the back of the head, the ears, and/or the neck of the welder. In an embodiment, FIGS. 1 and 2 illustrate a state in which the top of the head is covered by the auxiliary shield 20.

The auxiliary shield 20 may include a plurality of portions. In a first mode, the plurality of portions overlap each other. In a second mode, the overlapping state thereof is released, or the overlapping areas may be relatively reduced. In an embodiment, the auxiliary shield 20 may have a zigzag surface as illustrated in FIGS. 1 to 3, and while maintaining the zigzag surface, the portions positioned on both sides of a boundary line (or a folding line) may overlap each other.

For example, as illustrated in FIG. 3, the auxiliary shield 20 may have a structure in which portions, such as a first portion 21, a second portion 22 connected to the first portion 21, and a third portion 23 connected to the second portion 22, are connected to each other. Also, a boundary line (or a folding line) may be positioned between the neighboring portions. The first and second portions 21 and 22, which neighbor each other, may be folded to overlap each other along a folding line therebetween, and the second and third portions 22 and 23, which neighbor each other, may be folded to overlap each other along a folding line therebetween. As described above, as the neighboring portions are folded to overlap each other, the length of the auxiliary shield 20 may be reduced.

The auxiliary shield 20 being shortened may be positioned inside the face shield 10 as illustrated in FIG. 4. The portions that form the zigzag surface of the auxiliary shield 20 may be provided inside the face shield 10 while being folded to overlap each other.

As illustrated in FIG. 2, one portion 20A of the auxiliary shield 20 may be fixed to the inside of the main body 11 while overlapping an end of the main body 11 of the face shield 10. Also, as illustrated FIG. 4, the other portions of the auxiliary shield 20 may be accommodated inside the main body 11 while folded to overlap each other. The auxiliary shield 20 is positioned to overlap the main body 11 of the face shield 10 as illustrated in FIG. 4 (a first mode) and then may extend outward from one side of the main body 11 according to the needs of the welder as illustrated in FIG. 2 (a second mode). When switching from the first mode to the second mode, each of the portions of the auxiliary shield 20 may be released from the overlapping neighboring portion, or the overlapping areas may be reduced.

The auxiliary shield 20 may include a hard material. The hard material refers to a material capable of maintaining a shape thereof as long as an external force is not applied and is distinguished from fabric, as described above. The auxiliary shield 20 may include at least one of metal and plastic. In an embodiment, the auxiliary shield 20 may include a material resistant to heat that may be generated during welding and/or an external impact. For example, the auxiliary shield 20 may include heat-resistant plastic and/or reinforced plastic. The auxiliary shield 20 may include the same material as the main body 11 or a different material from the main body 11. Also, the auxiliary shield 20 may include a film having a certain shape. For example, the auxiliary shield 20 may include a polymer film in which folding lines between the neighboring portions may be identified with the naked eyed. The polymer described above is distinguished from a high strength film which breaks without shape deformation when an external force is applied, and may be a polymer which is deformed into another shape when an external force is applied and restored to its original shape due to an external force that is applied in a direction opposite to the above-described external force.

When the welding protector 1 is stored or carried by the welder in a state in which the auxiliary shield 20 is exposed to the outside, the auxiliary shield 20 is damaged, or the storability and portability of the welding protector 1 is degraded. However, as in the embodiments of the present disclosure, because the portions of the auxiliary shield 20 are accommodated inside the face shield 10 while overlapping each other, the limitation described above may be prevented or reduced. Also, the auxiliary shield 20 may be prevented from being exposed to external pollutants and the like, and thus, the durability of the auxiliary shield 20 may be enhanced.

Figure 5:
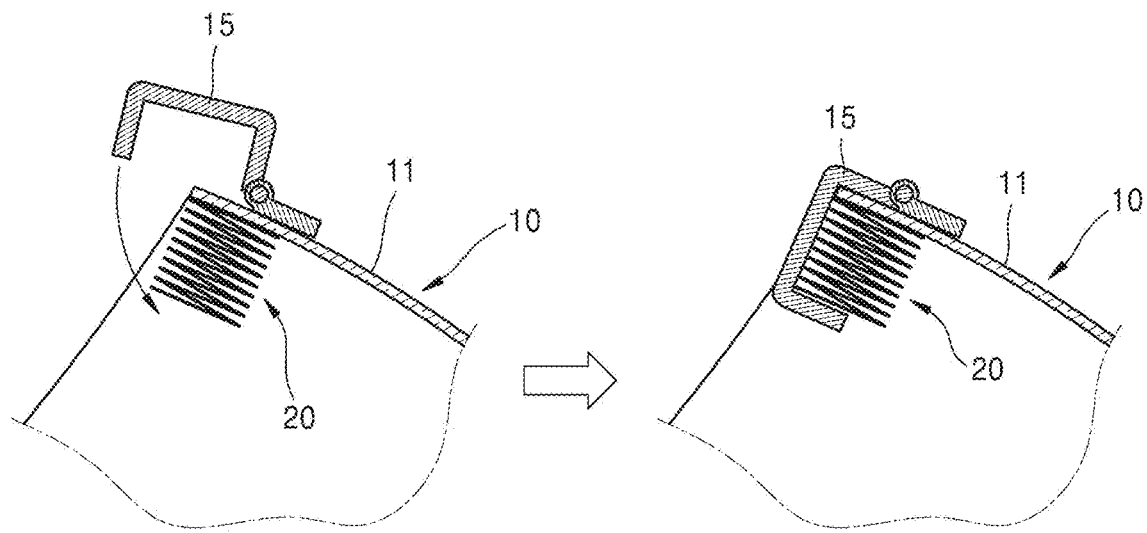
FIGS. 5 and 6 are side cross-sectional views of a portion of the welding protector according to an embodiment of the present disclosure.
Figure 6:
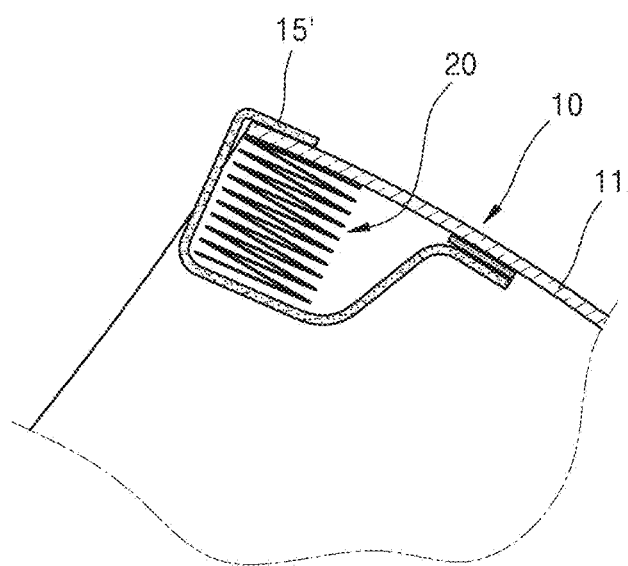

FIGS. 5 and 6 are side cross-sectional views of a portion of the welding protector according to an embodiment of the present disclosure. Referring to FIG. 5, an auxiliary shield 20 may be provided inside a face shield 10 in a state where the neighboring portions are folded to overlap each other as described above with reference to FIG. 4, and the position of the auxiliary shield 20 provided inside the face shield 10 may be fixed by a fixing member 15.

In an embodiment, FIG. 5 illustrates that the fixing member 15 is a hinge type. One side of the fixing member 15 of a hinge-type is fixed to the top surface of a main body 11 of the face shield 10, and the other side thereof rotates, thereby fixing the position of the auxiliary shield 20.

In another embodiment, a fixing member 15' may include a rigid or flexible strip and the like as illustrated in FIG. 6. In a state where one end of the fixing member 15' is fixed to the outside of the face shield 10, the other end is fixed to a member provided inside the main body 11 in a Velcro-like manner or using a snap button and the like.

In some embodiments, a fixing member 15 may be fixed to the inside of the face shield 10 in an insertion manner using a structure of a protrusion and groove. As in the embodiments described above, detail structures and fixing methods for the fixing member 15 may diversely change.

Figure 7:
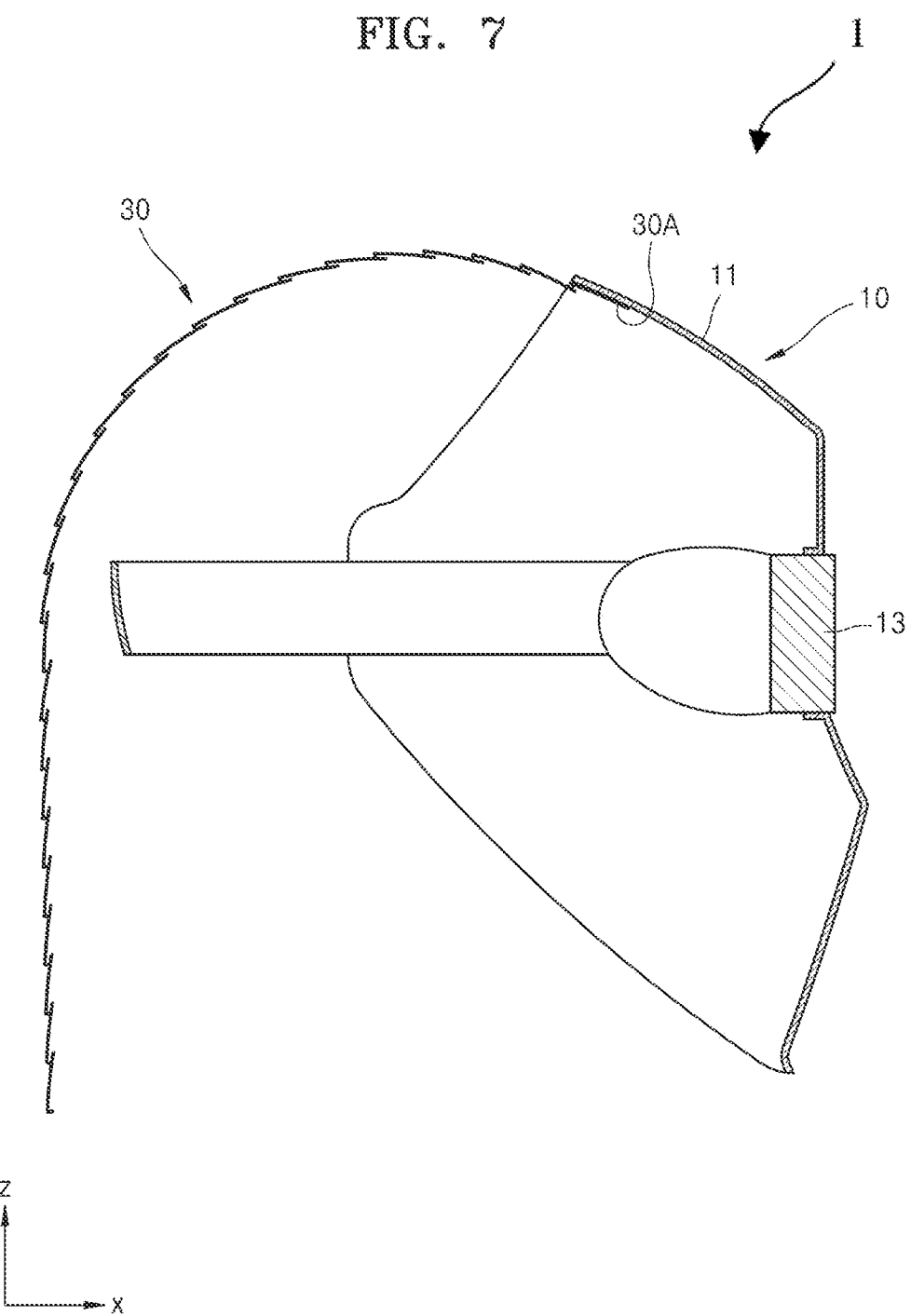
FIG. 7 is a schematic side cross-sectional view of a welding protector according to an embodiment of the present disclosure.
Figure 8:
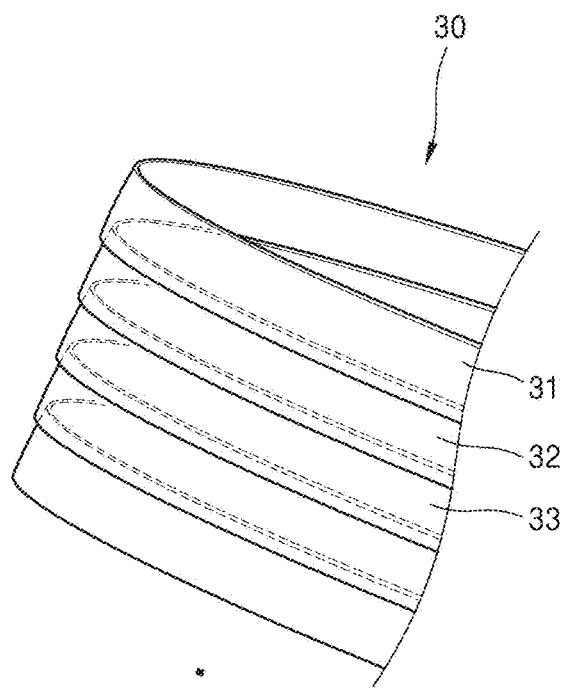
FIG. 8 is a perspective view of a portion extracted from an auxiliary shield according to an embodiment of the present disclosure.
Figure 9:
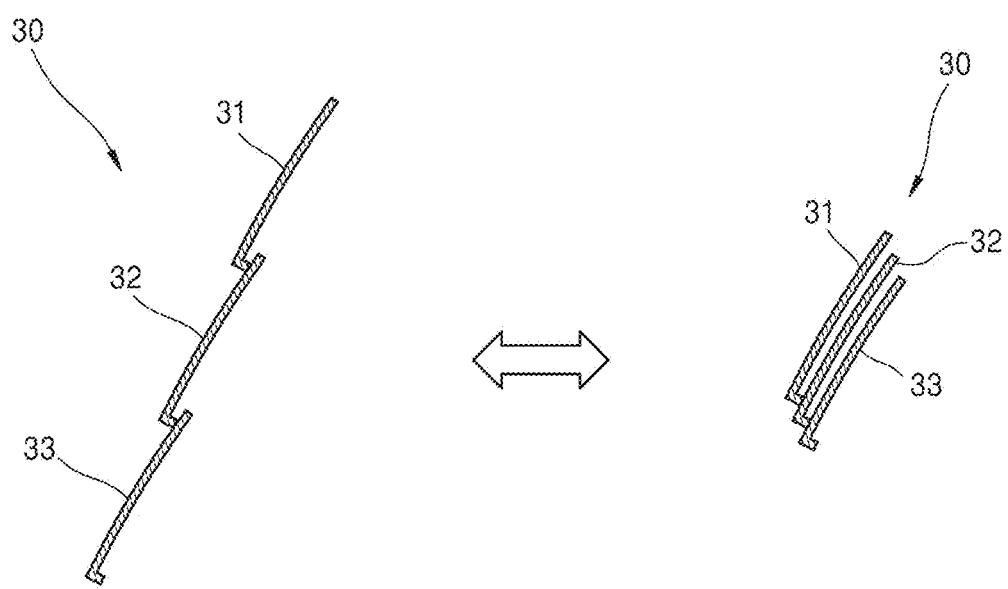
FIG. 9 is a side cross-sectional view showing an overlapping state of an auxiliary shield that corresponds to a part of FIG. 8.
Figure 10:
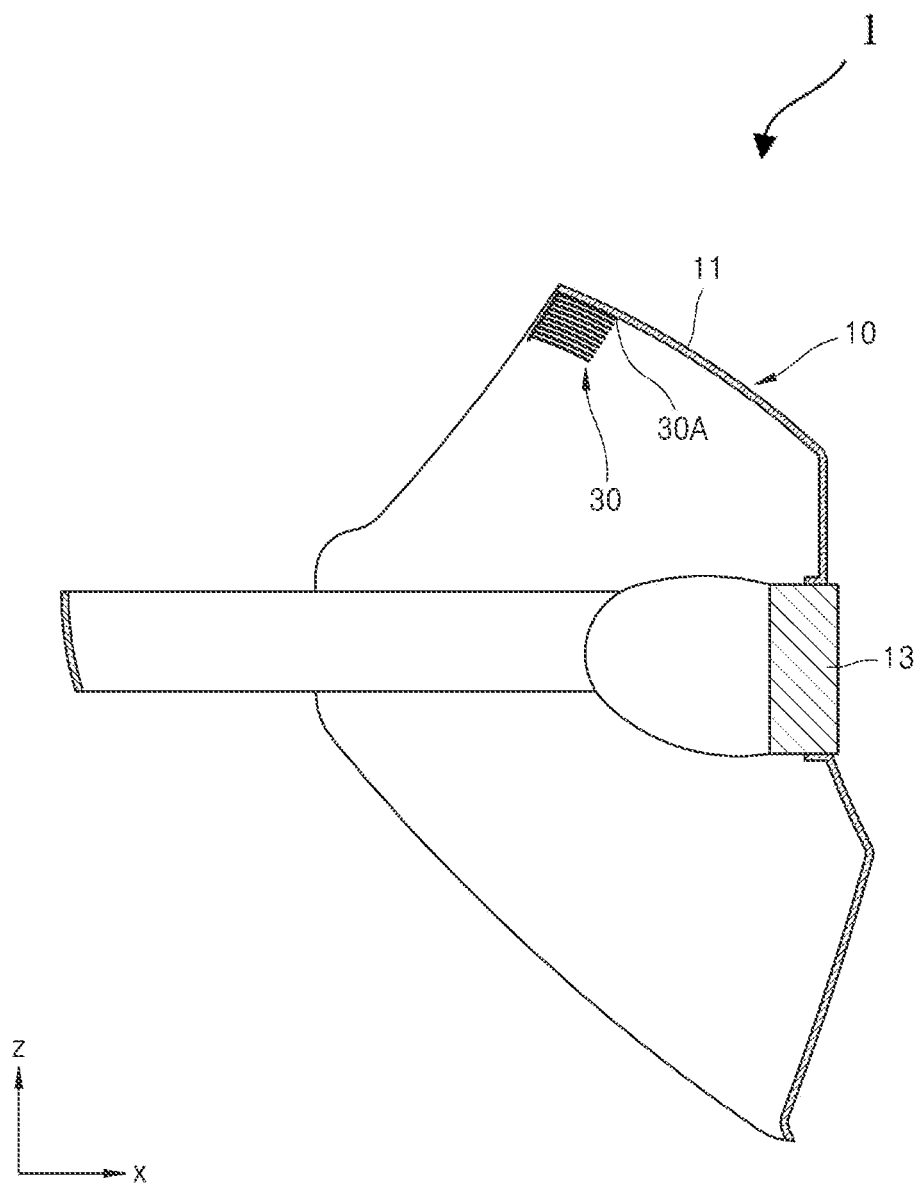
FIG. 10 is a schematic side cross-sectional view of a welding protector according to still an embodiment.
Figure 11:
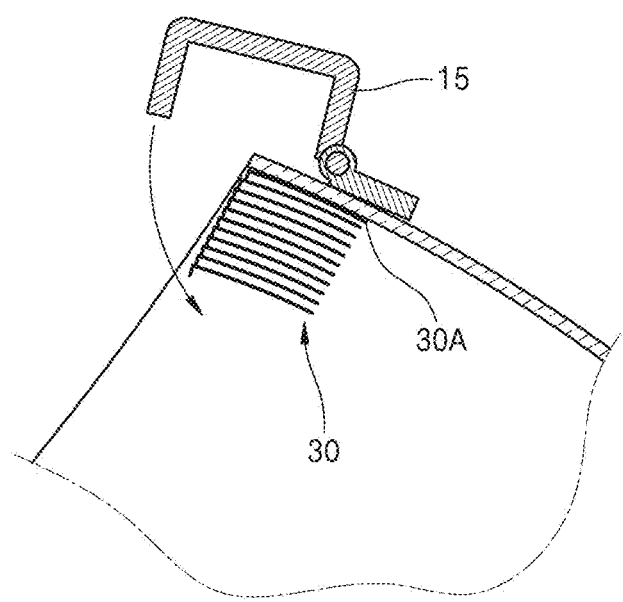
FIG. 11 is a side cross-sectional view of a portion of a welding protector according to an embodiment of the present disclosure.

FIG. 7 is a schematic side cross-sectional view of a welding protector according to an embodiment of the present disclosure, FIG. 8 is a perspective view of a portion extracted from an auxiliary shield according to an embodiment of the present disclosure, FIG. 9 is a side cross-sectional view showing an overlapping state of an auxiliary shield that corresponds to a part of FIG. 8, FIG. 10 is a schematic side cross-sectional view of a first mode in a welding protector according to an embodiment of the present disclosure, and FIG. 11 is a schematic side cross-sectional view showing that a welding protector includes a fixing member.

Referring to FIG. 7, a welding protector 1 may include a face shield 10 and an auxiliary shield 30. The face shield 10 of FIG. 7 is the same as the face shield described with reference to FIG. 1, etc., hereinafter the auxiliary shield 30 will be mainly described.

The auxiliary shield 30 may cover another portion of the body of a welder which are not covered by the face shield 10, for example, the top of the head part, the back of the head, the ears, and/or the neck region. In an embodiment, FIGS. 7 to 11 illustrate that the auxiliary shield 30 covers the top of the head part of the welder. The auxiliary shield 30 may extend from an edge of the face shield 10 and cover the top of the head part of the welder.

The auxiliary shield 30 includes a plurality of portions, and when switching from a first mode to a second mode, each of the portions may linearly move with respect to the neighboring portion. For example, each portion may linearly move with respect to the neighboring portion in a direction away from the face shield 10. For example, the portions of the auxiliary shield 30 may slide along a direction. For example, the auxiliary shield 30 may include a first portion 31, a second portion 32, and a third portion 33, which are adjacent to each other as illustrated in FIG. 8. The second portion 32 may linearly slide on the first portion 31, and the third portion 33 may linearly slide on the second portion 32.

The position of each portion of the auxiliary shield 30 relative to the neighboring portion changes when sliding, but the shape of each portion itself may be maintained. For example, each of the portions constituting the auxiliary shield 30 may include polymer capable of maintaining the shape thereof. For example, each portion of the auxiliary shield 30 may include a polymer film having a predetermined strength.

When switching from the first mode to the second mode, each of the portions constituting the auxiliary shield 30 may decrease in overlapping area. As illustrated in FIG. 9, the overlapping area of the second portion 32 with the first portion 31 may be reduced when switching from the first mode to the second mode, and the overlapping area may increase when switching from the second mode to the first mode. Similarly, the third portion 33 may linearly move to reduce an overlapping area with the second portion 32 when switching from the first mode to the second mode, and may linearly move to increase the overlapping area when switching from the second mode to the first mode. As the overlapping area of the first portion 31 and the second portion 32 and the overlapping area of the second portion 32 and the third portion 33 increase, the length of the auxiliary shield 30 may be reduced.

An end portion 30A of the auxiliary shield 30 may be fixed to the inside of the face shield 10 as illustrated in FIGS. 7 and 10. The auxiliary shield 30, which is folded as illustrated in FIG. 10, may be accommodated inside the face shield 10 while positioned on the end portion 30A. The position of the auxiliary shield 30 accommodated inside the face shield 10 may be fixed by a fixing member 15 as illustrated in FIG. 11.

FIG. 11 illustrates that the fixing member 15 is a hinge type. One side of the fixing member 15 is fixed to the top surface of a main body 11 of the face shield 10, and the other side thereof rotates, thereby fixing the position of the auxiliary shield 30. However, the embodiment of the present disclosure is not limited thereto. In another embodiment, the fixing member 15' having the rigid or flexible strip and the like described with reference to FIG. 6 may be fixed using Velcro, a snap button, or the like. As long as the position of the folded auxiliary shield 30 is capable of being fixed to the face shield 10, a structure or method in which the fixing member 15' fixes the auxiliary shield 30 may be diversely modified.

Figure 12:
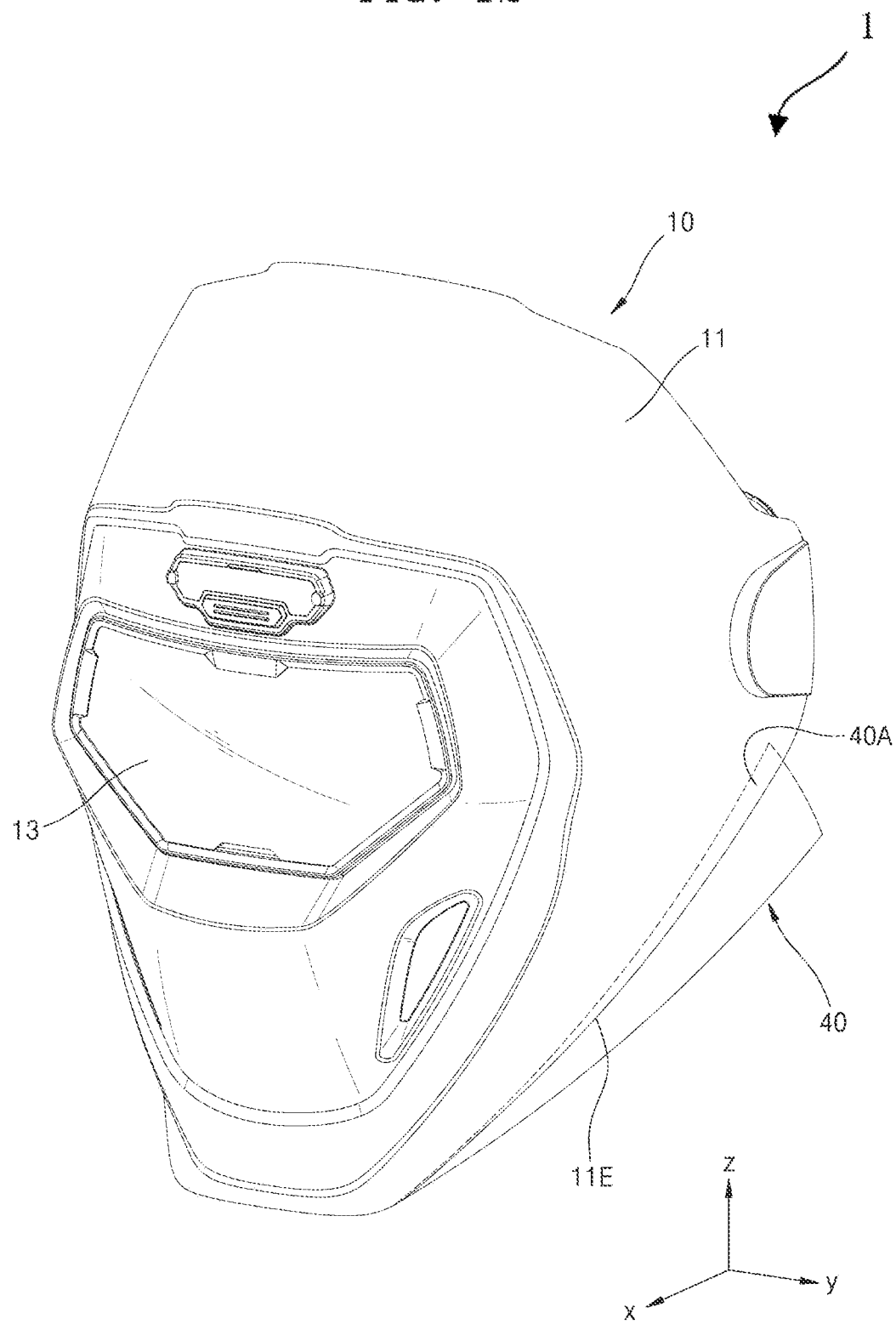
FIG. 12 is a perspective view of a welding protector according to an embodiment of the present disclosure.
Figure 13:
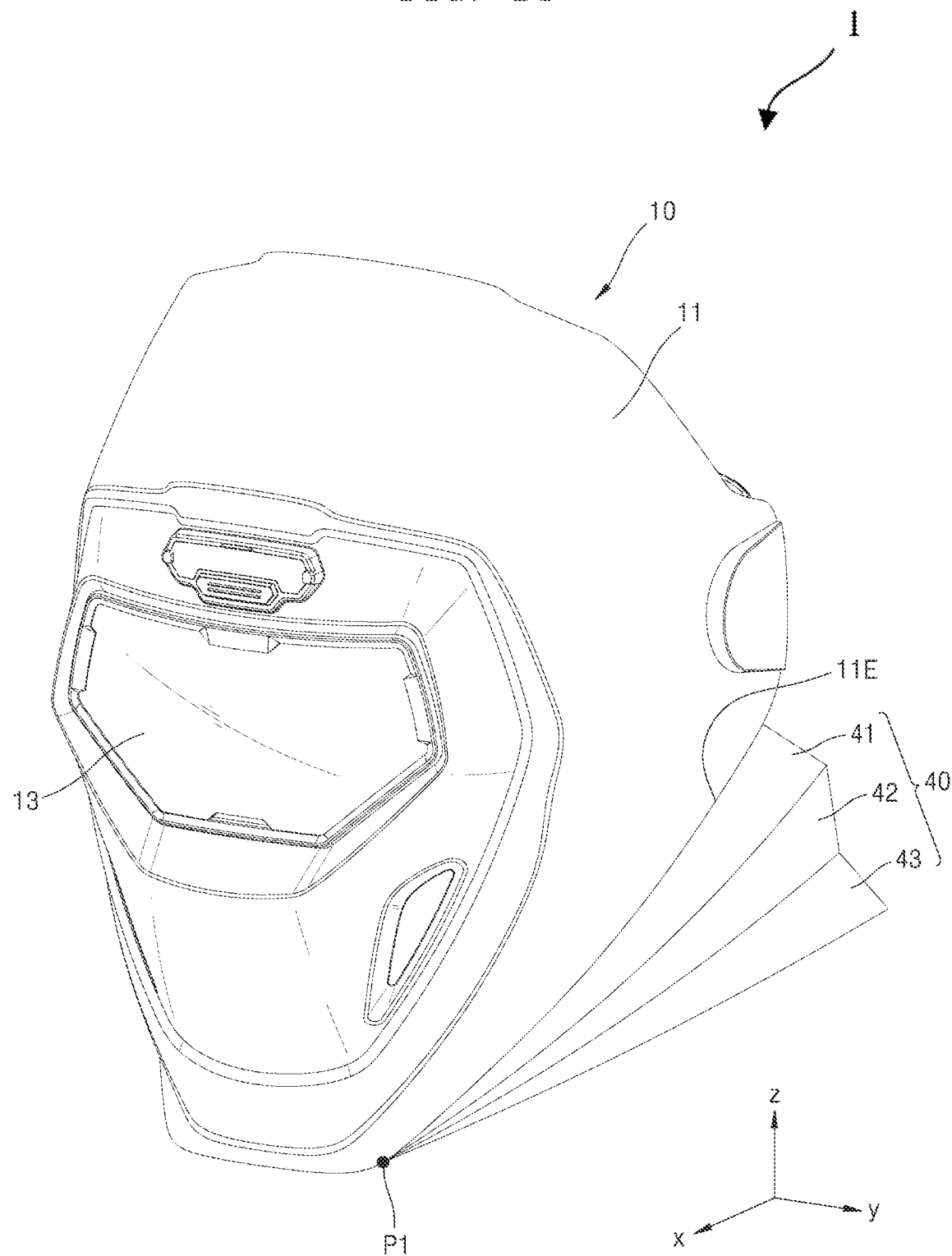
FIG. 13 shows a state in which an auxiliary shield of FIG. 12 is moved.

FIG. 12 is a perspective view of a welding protector according to an embodiment of the present disclosure, and FIG. 13 shows a state in which an auxiliary shield of FIG. 12 is moved.

Referring to FIGS. 12 and 13, a welding protector 1 includes a light blocking member 13 capable of protecting the eyes of a welder and a main body 11 surrounding the periphery of the light blocking member 13. An auxiliary shield 40 is positioned on one side of the main body 11. The main body 11 may include a first edge 11E corresponding to the jaw of the welder. The auxiliary shield 40 may be positioned to be adjacent to the first edge 11E of the main body 11. FIG. 12 is a perspective view illustrating one first edge 11E, but a pair of first edges 11E may be provided, forming an approximate V shape with respect to the face of the welder to correspond to the jaw of the welder. One end portion 40A of the auxiliary shield 40 may be fixed to the first edge 11E of a main body 11 or around the first edge 11E.

The auxiliary shield 40 may be close to the first edge 11E of a face shield 10 in a first mode as illustrated in FIG. 12, for example, may be positioned to partially overlap a portion having the first edge 11E of the face shield 10. The auxiliary shield 40 may be unfolded in a second mode as illustrated in FIG. 13 to protect the neck region of the welder.

In an embodiment, FIG. 13 illustrates that the auxiliary shield 40 includes portions 41, 42, and 43 that constitute a zigzag surface. The portions 41, 42, and 43 may be at least partially accommodated inside the face shield 10 while overlapping each other as illustrated in FIG. 12 when the welding protector 1 is stored or when the auxiliary shield 40 is not used. In an embodiment, as illustrated in FIG. 13, each of the portions 41, 42, and 43 may have a shape, in which an area is gradually reduced toward one end, for example, a triangular shape. Each of the portions 41, 42, and 43 may be unfolded and folded around a first point P1 adjacent to a triangular vertex. The width of the auxiliary shield 40, for example, when the auxiliary shield 40 is unfolded, the maximum width may be in a range from about 1 cm to about 10 cm.

The first point P1 is a place, where ends of the portions 41, 42, and 43 of the auxiliary shield 40 meet each other, and serves as a axis when the auxiliary shield 40 is unfolded and folded. The ends of the portions 41, 42, and 43 of the auxiliary shield 40 are fixed ends, and for example, may be fixed at the first point P1.

FIG. 13 illustrates that the auxiliary shield 40 protecting the neck region of the welder includes the portions 41, 42, and 43 forming the zigzag surface as described with reference to FIG. 1, etc. However, in another embodiment, the plurality of portions are not integrally connected to each other as illustrated in FIG. 14.

Figure 14:
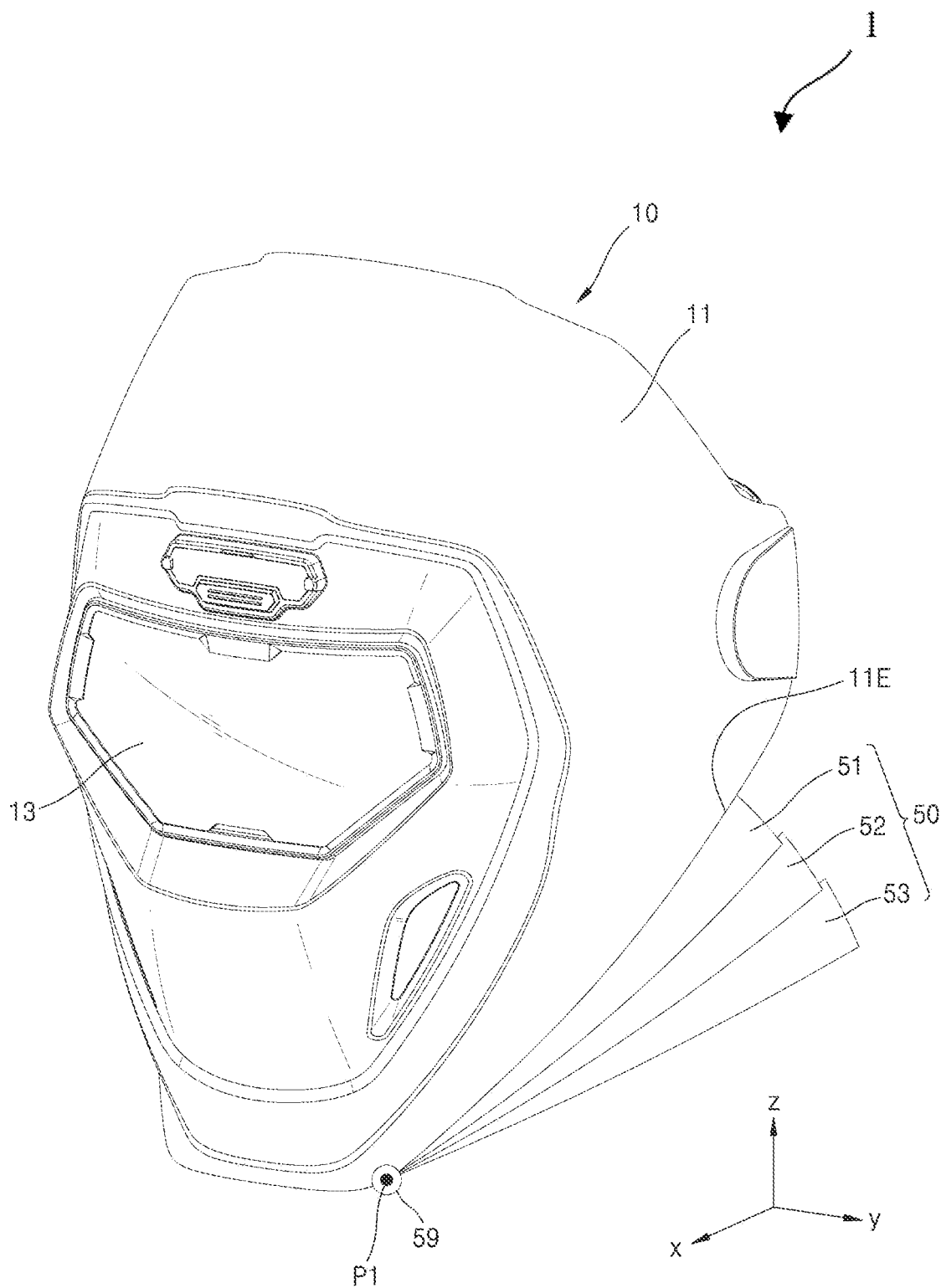
FIG. 14 is a perspective view of a welding protector according to an embodiment of the present disclosure.

FIG. 14 is a perspective view of a welding protector according to an embodiment of the present disclosure.

As illustrated in FIG. 14, an auxiliary shield 50 may include a plurality of portions 51, 52, and 53 that may rotate around an axis passing through a first point P1. In this case, each of the portions 51, 52, and 53 may rotate a predetermined angle around a coupling portion 59 corresponding to the first point P1 and protect the neck region of the welder. The coupling portion 59 or the first point P1 may be a rotation axis or a coupling axis of each of the portions 51, 52, and 53. For example, ends of the portions 51, 52, and 53 of the auxiliary shield 50 may be fixed at the first point P1 and/or the coupling portion 59 and coupled to each other.

FIGS. 12 to 14 illustrate that the auxiliary shield for protecting the neck region of the welder is positioned inside the main body 11 having the first edge 11E, but the embodiment of the present disclosure is not limited thereto. The auxiliary shield may be positioned on the outer surface adjacent to the first edge 11E of the main body 11 (for example, a position corresponding to the cheek of the welder or the like). In this case, the auxiliary shield may be positioned on the outer surface of the main body 11, and the first point P1 and/or the coupling portion 59 may also be positioned on the outer surface of the main body 11.

FIGS. 12 and 14 illustrate the auxiliary shield that covers the neck region of the welder. In another embodiment, however, the auxiliary shield may be at a position, adjacent to one edge of the main body 11 and corresponding to the ears of the welder, to protect the ear region of the welder.

Figure 15:
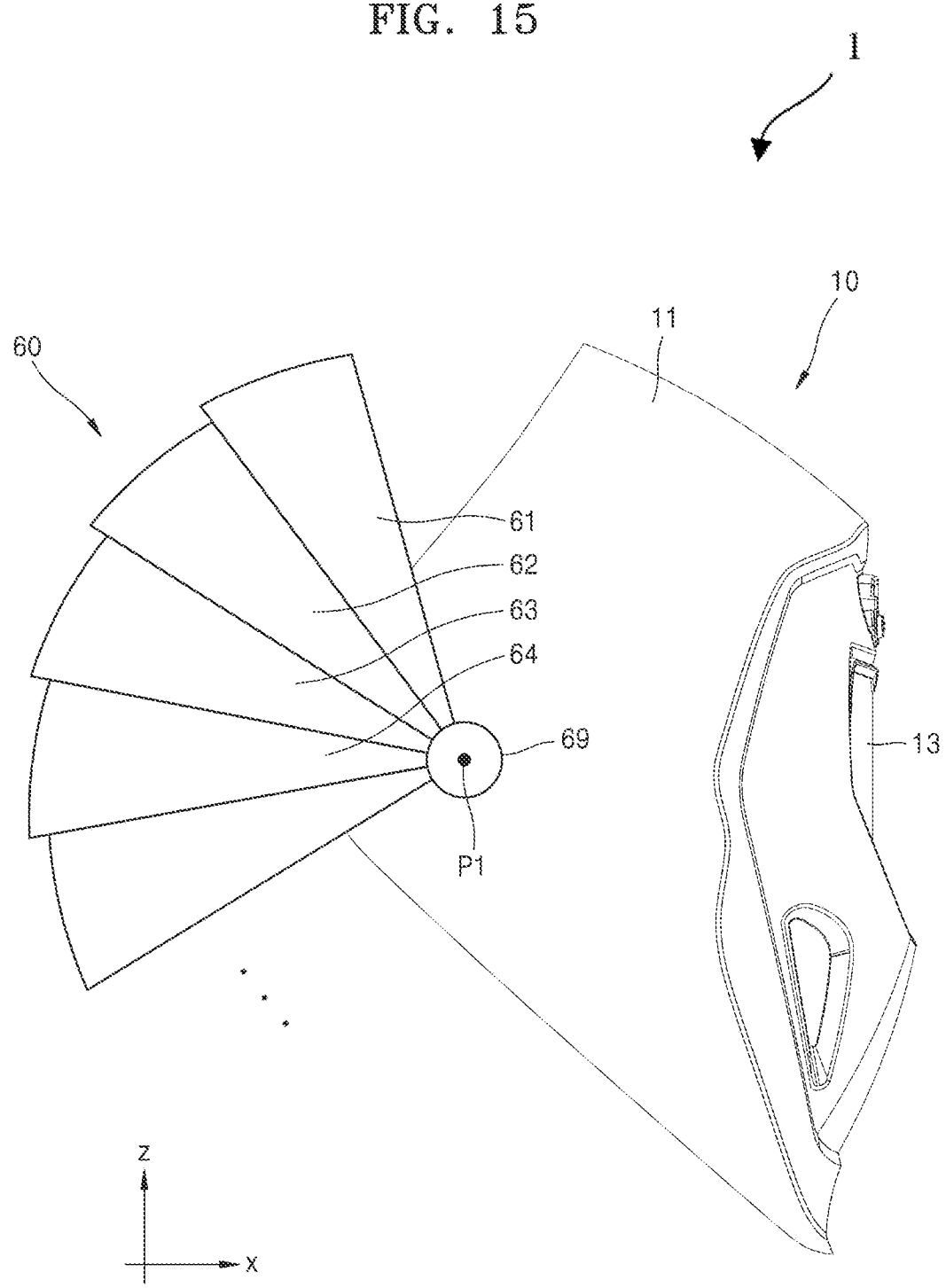
FIG. 15 is a perspective view of a welding protector according to an embodiment of the present disclosure.
Figure 16:
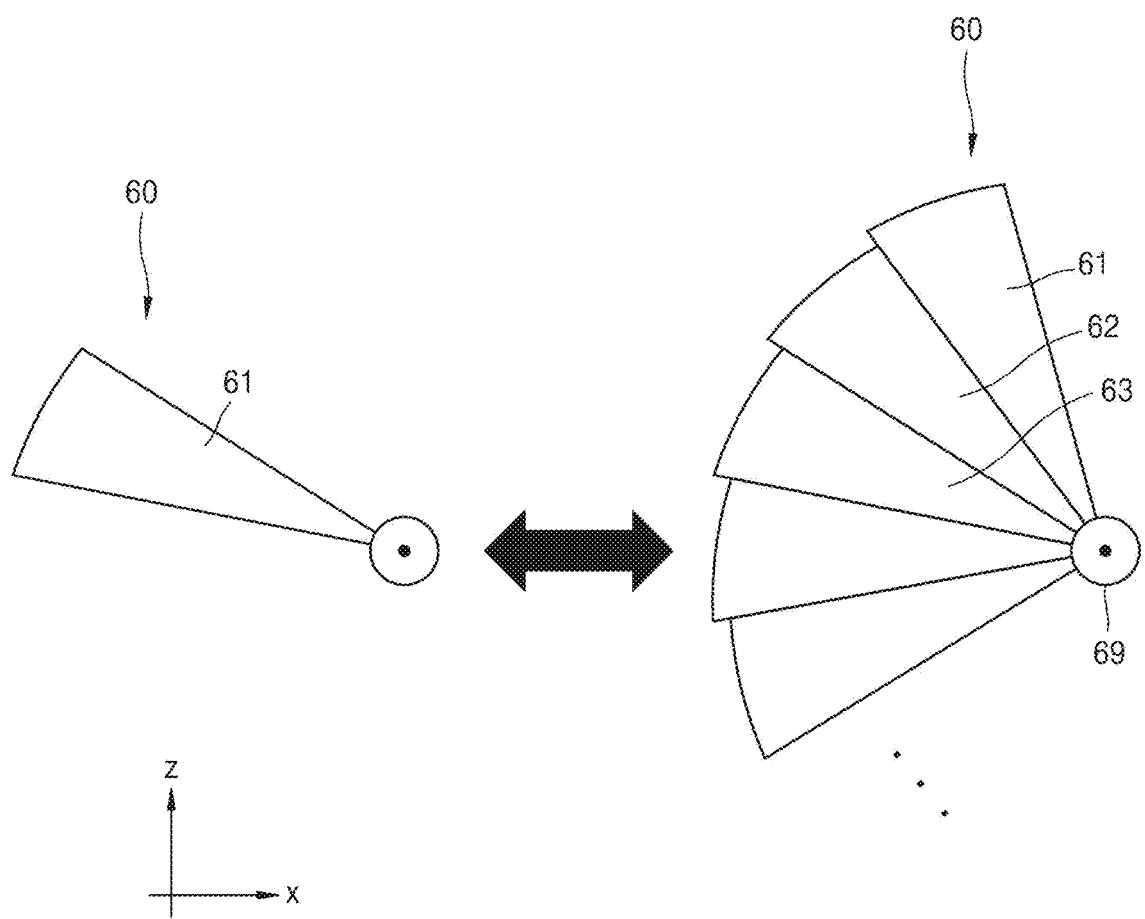
FIG. 16 is a side view of an auxiliary shield extracted from FIG. 15.

FIG. 15 is a perspective view of a welding protector according to an embodiment of the present disclosure, and FIG. 16 is a side view of an auxiliary shield extracted from FIG. 15.

Referring to FIG. 15, an auxiliary shield 60 may protect the ear region of the welder. For example, as illustrated in FIG. 15, the auxiliary shield 60 may extend to cover a region corresponding to the ears of the welder and the head part of the welder between the ears, for example, the back of the head. In another embodiment, portions corresponding to both ears of the welder are spaced apart from each other, and thus, the back of the head of the welder between the ears may not be covered. FIG. 15 illustrates a plurality of portions 61, 62, 63, and 64 as an embodiment.

The plurality of portions 61, 62, 63, and 64 may rotate around a pair of coupling portions 69 positioned on a main body 11 as illustrated in FIG. 16. The plurality of portions 61, 62, 63, and 64 may rotate around an axis passing through the pair of coupling portions 69. For example, one of the neighboring portions may rotate, with respect to the other one, around the axis passing through the pair of coupling portions 69. Thus, in a second mode, the auxiliary shield 60 may increase in area. In a case where a welding operation is not performed, one of the neighboring portions included in the auxiliary shield 60 may rotate, with respect to the other one, around the axis passing through the pair of coupling portions 69. That is, the one portion may rotate to increase the overlapping area between the neighboring portions (a first mode). Thus, the area, to be covered by the auxiliary shield 60, in a portion of the body of the welder may be reduced.

In an embodiment, FIGS. 15 and 16 illustrate that the coupling portion 69 is on the outer surface of the main body 11. In another embodiment, however, the coupling portion 69 may be on the inner surface of the main body 11. The auxiliary shield 60 may be fixed to the main body 11, and in an embodiment, the welding protector may be further provided with the fixing members described with reference to FIGS. 5, 6, and 11, etc.

Figure 17:
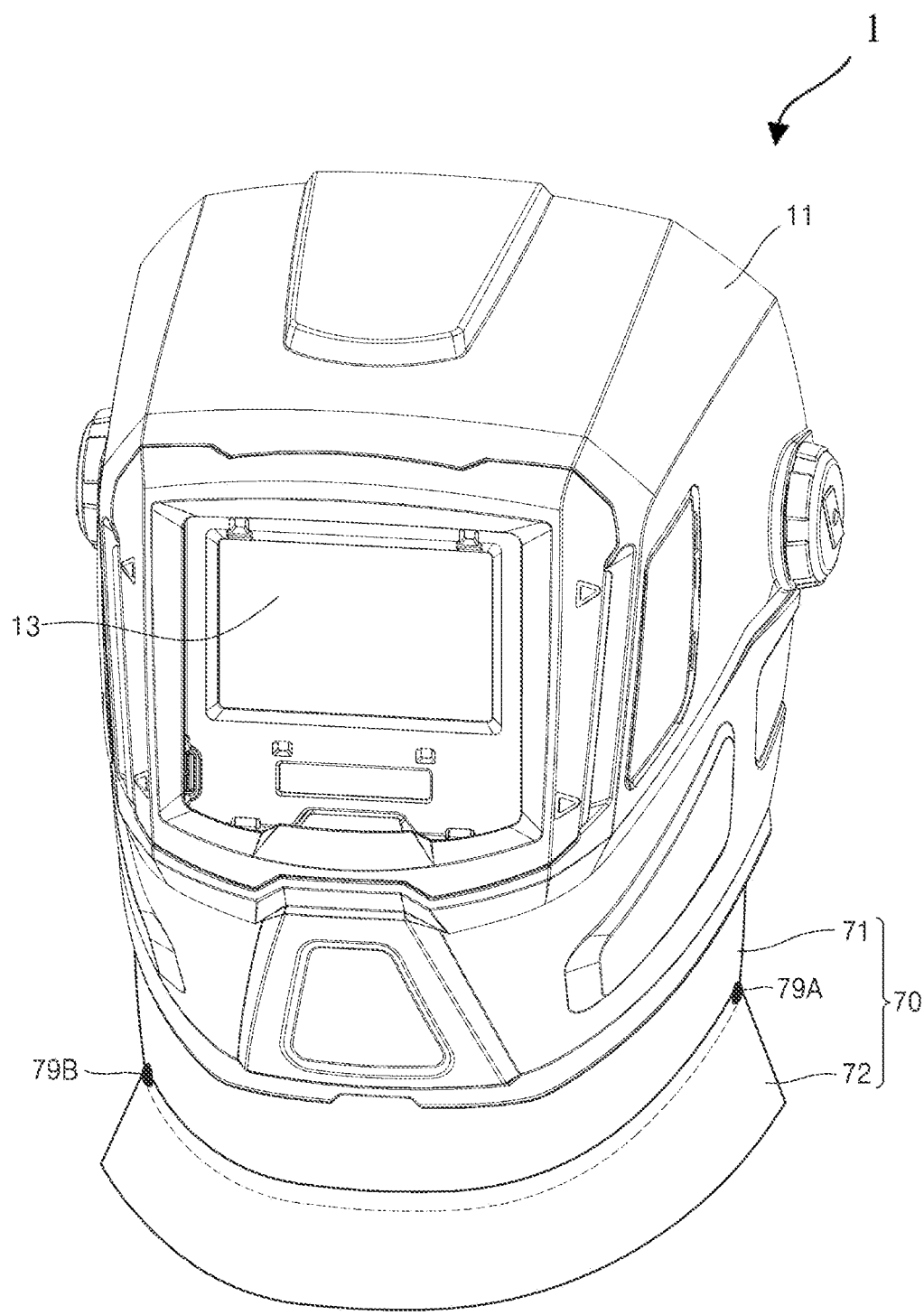
FIG. 17 is a perspective view of a protector according to an embodiment of the present disclosure.
Figure 18A:
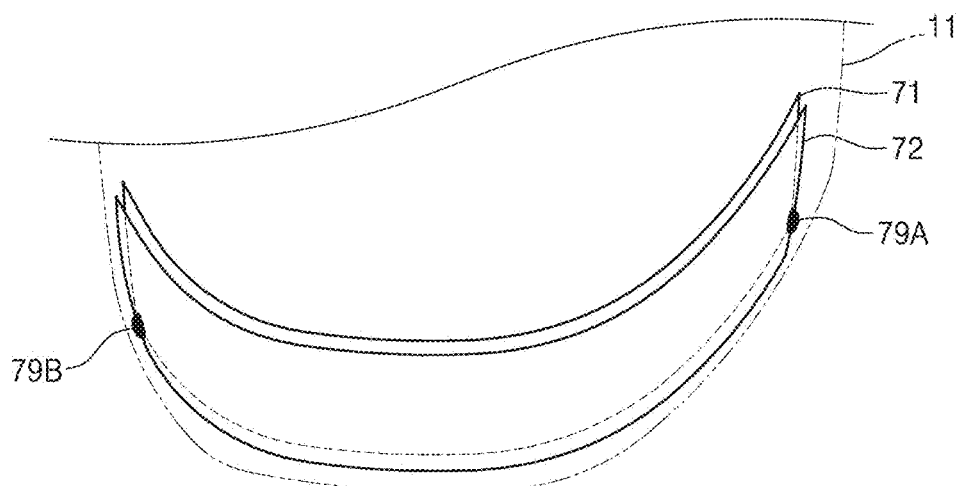
FIGS. 18A to 18C are perspective views showing a movement of an auxiliary shield of FIG. 17.
Figure 18B:
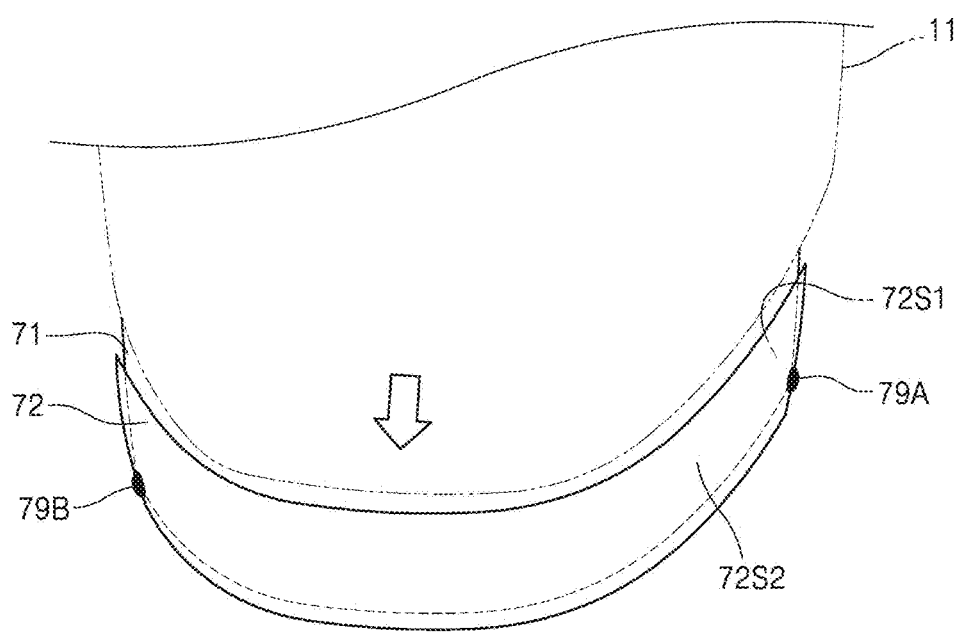
Figure 18C:
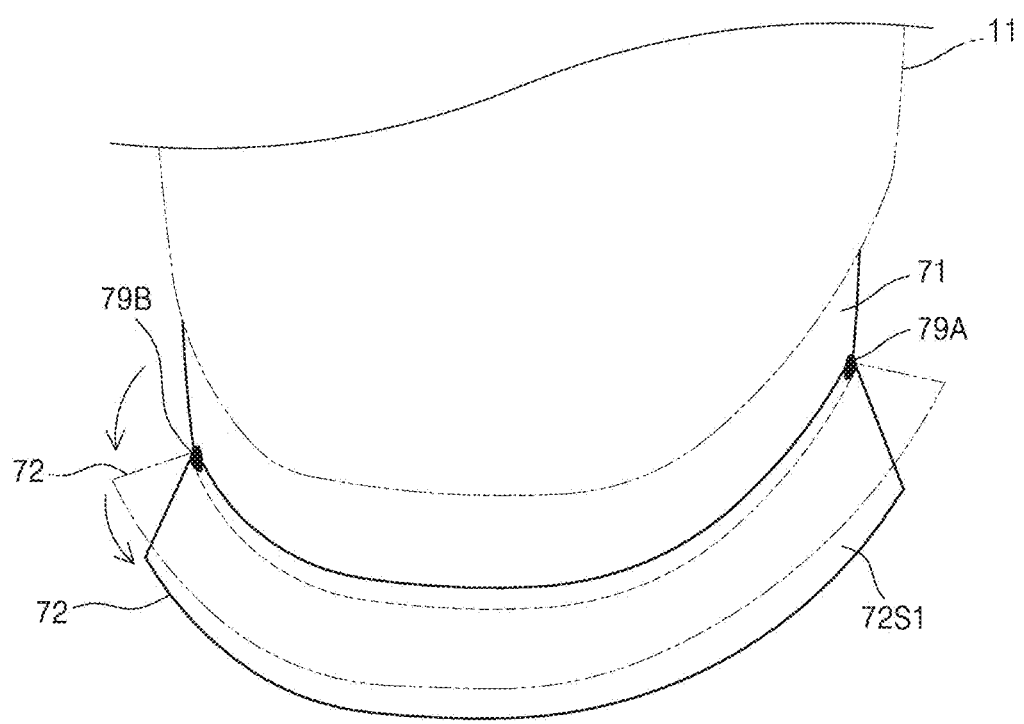

FIG. 17 is a perspective view of a protector according to an embodiment of the present disclosure, and FIGS. 18A to 18C are perspective views showing a movement of an auxiliary shield of FIG. 17.

Referring to FIG. 17, an auxiliary shield 70 may protect the neck region of the welder. The auxiliary shield 70 may include a plurality of portions. In an embodiment, FIG. 17 illustrates that the auxiliary shield 70 includes a first portion 71 and a second portion 72.

The first portion 71 and the second portion 72 may include a hard material to have a predetermined shape. The hard material refers to a material capable of maintaining a shape thereof as long as an external force is not applied and is distinguished from fabric. The auxiliary shield 70 may include at least one of metal and plastic. In an embodiment, the auxiliary shield 70 may include a material resistant to heat that may be generated during welding and/or an external impact. For example, the auxiliary shield 70 may include heat-resistant plastic and/or reinforced plastic. The auxiliary shield 70 may include the same material as a main body 11 or a different material from the main body 11. Also, the auxiliary shield 70 may include a material having a shape which is deformed by an external force and restored again by an external force, for example, a polymer film. The width of the auxiliary shield 70, for example, the maximum width may be selected in a range from about 1 cm to about 10 cm. For example, the width of the auxiliary shield 70 may be selected in a range from about 1 cm to about 5 cm.

As illustrated in FIG. 18A, the auxiliary shield 70 may be positioned inside the main body 11 of a welding protector 1 (a first mode). In the auxiliary shield 70 accommodated inside the main body 11, a first portion 71 and a second portion 72 may overlap each other.

When switching from the first mode to a second mode, the auxiliary shield 70 moves linearly as a whole and may be exposed to the outside of the main body 11 of the welding protector 1 as illustrated in FIG. 18B (a second-first mode). Subsequently, in a direction away from the first portion 71, the second portion 72 may rotate around an axis passing through a first coupling portion 79A and a second coupling portion 79B as illustrated in FIGS. 18B and 18C (a second-second mode). For example, the auxiliary shield 70 may linearly move with respect to the main body 11 through a structure of a guide groove and a guide protrusion coupled to the guide groove and come out of a face shield 10. Subsequently, the second portion 72 rotates around an axis (for example, the axis passing through the first coupling portion 79A and the second coupling portion 79B) and is unfolded. As a result, the area of the auxiliary shield 70 may increase. Through such a series of operations, the neck region of the welder may be protected by the auxiliary shield 70. The operations of the second-first mode described above and the specific configuration thereof may be applied in the same manner to the auxiliary shields according to the embodiments described above and/or auxiliary shields that will be described later.

In the second-first mode, a first surface 72S1 of the second portion 72 faces the welder (for example, the neck of the welder). In the second-second mode, as the second portion 72 rotates, the first surface 72S1 may be exposed to the outside as illustrated in FIG. 18C.

FIGS. 17 and 18A to 18C illustrate that the auxiliary shield 70 covers the neck region of the welder, but the structure of the auxiliary shield 70 described above may be applied to the ear region, the back region of the head, or the like of the welder.

Figure 19:
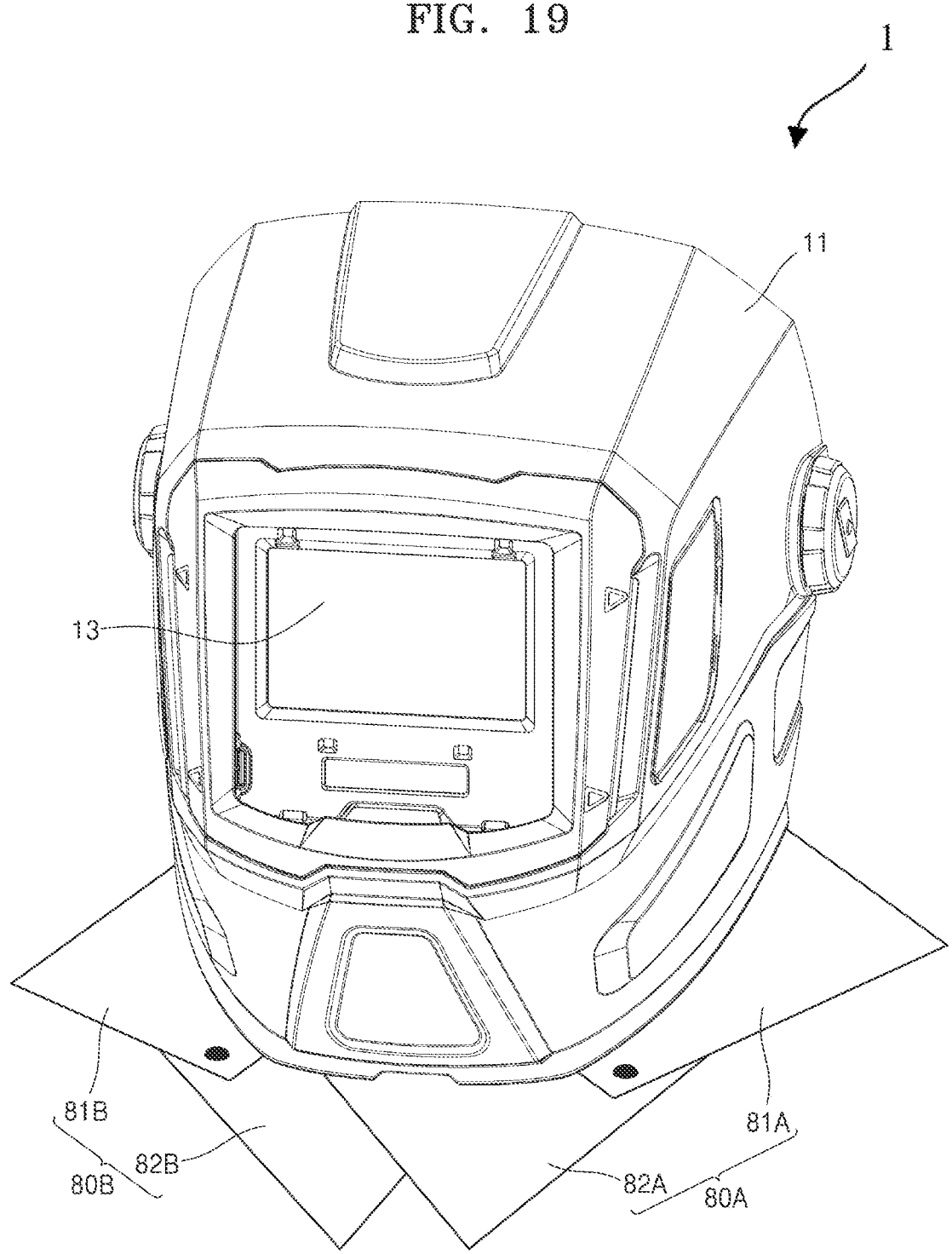
FIG. 19 is a perspective view of a protector according to an embodiment of the present disclosure.
Figure 20A:
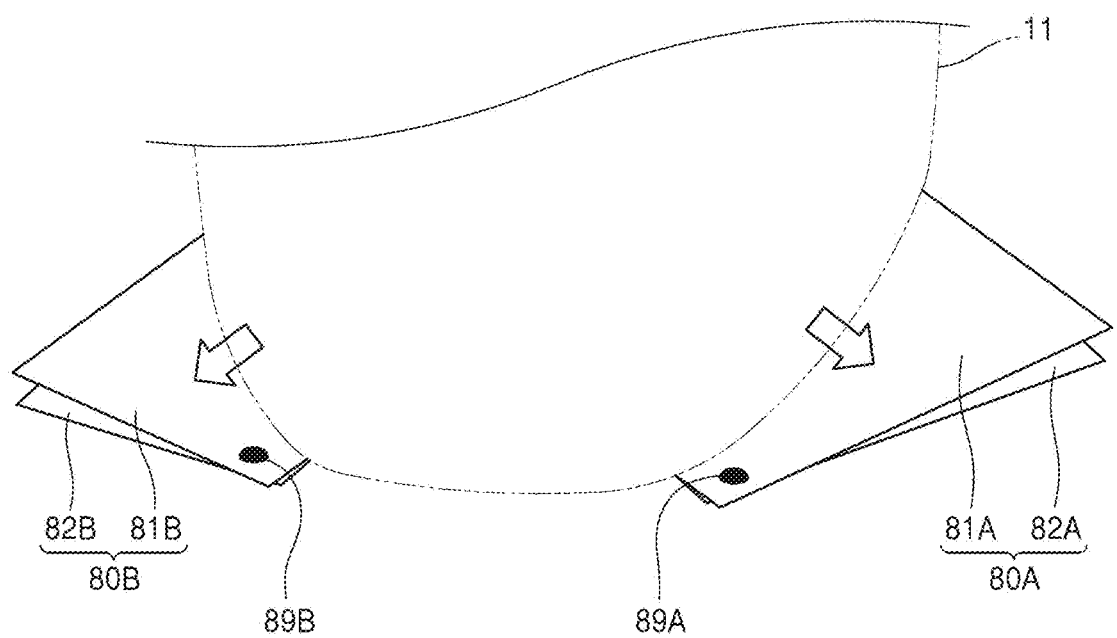
FIGS. 20A and 20B are perspective views showing movements of first and second auxiliary shields of FIG. 19.
Figure 20B:
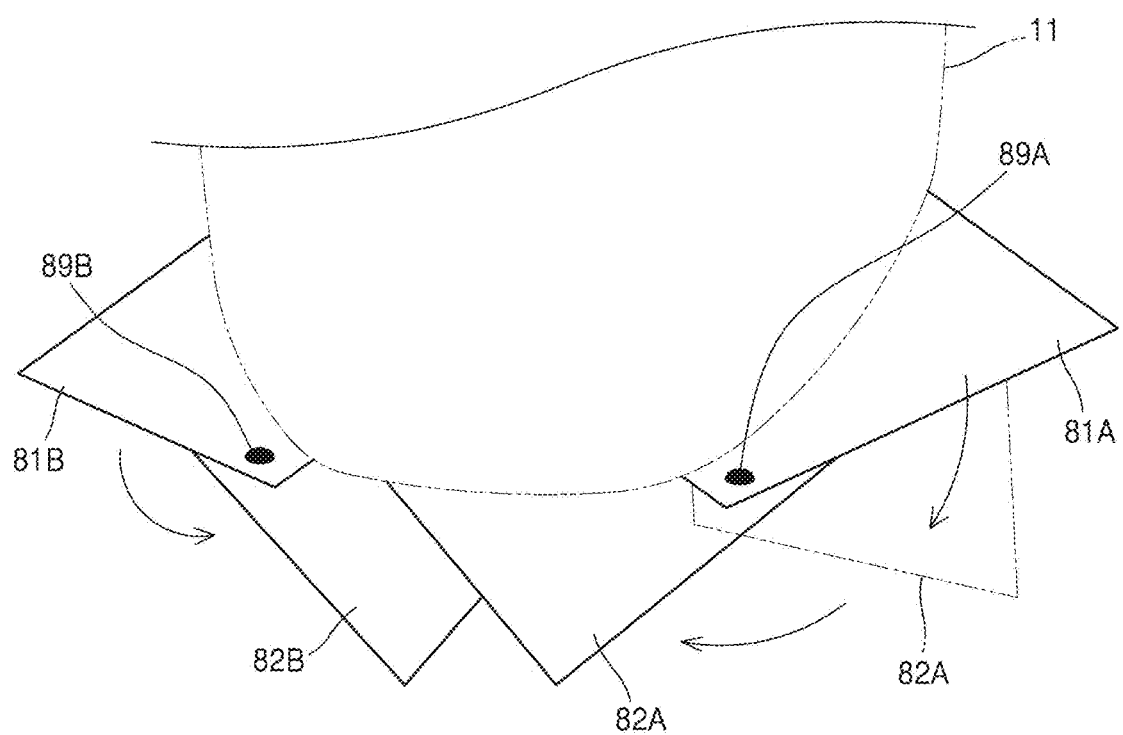

FIG. 19 is a perspective view of a protector according to an embodiment of the present disclosure, and FIGS. 20A and 20B are perspective views showing movements of first and second auxiliary shields of FIG. 19.

Referring to FIG. 19, a welding protector 1 may include a plurality of auxiliary shields. For example, the welding protector 1 may include a first auxiliary shield 80A and a second auxiliary shield 80B. In an embodiment, FIG. 19 illustrates each of the first auxiliary shield 80A and the second auxiliary shield 80B is positioned around the neck region in a main body 11 of the welding protector 1.

The first auxiliary shield 80A may include a first portion 81A and a second portion 82A, and the second auxiliary shield 80B may include a third portion 81B and a fourth portion 82B. The first and second portions 81A and 82A and the third and fourth portions 81B and 82B may be rigid enough to have a predetermined shape, and may include a material having a shape which is deformed when an external force is applied and restored again by an external force, for example, a polymer.

As illustrated in FIG. 20A, the first auxiliary shield 80A and the second auxiliary shield 80B positioned inside the main body 11 of the welding protector 1 may slide when necessary and move out of the main body 11 of the welding protector 1. The first portion 81A and the second portion 82A of the first auxiliary shield 80A accommodated in the main body 11 overlap each other, and the third portion 81B and the fourth portion 82B of the second auxiliary shield 80B overlap each other.

Subsequently, as illustrated in FIG. 20B, the second portion 82A rotates around a predetermined axis with respect to the first portion 81A to reduce an overlapping area with the first portion 81A, and thus, the neck region of the welder may be covered. For example, the second portion 82A may rotate around an axis passing through a first coupling portion 89A.

Similarly, the fourth portion 82B rotates with respect to the third portion 81B to reduce an overlapping area with the third portion 81B, and thus, the neck region of the welder may be covered. For example, the fourth portion 82B may rotate around an axis passing through a second coupling portion 89B.

FIGS. 19, 20A, and 20C illustrate that the first and second auxiliary shields 80A and 80B cover the neck region of the welder, but the structure of the first and second auxiliary shields 80A and 80B described above may be applied to the ear region, the back region of the head, or the like of the welder.

Figure 21:
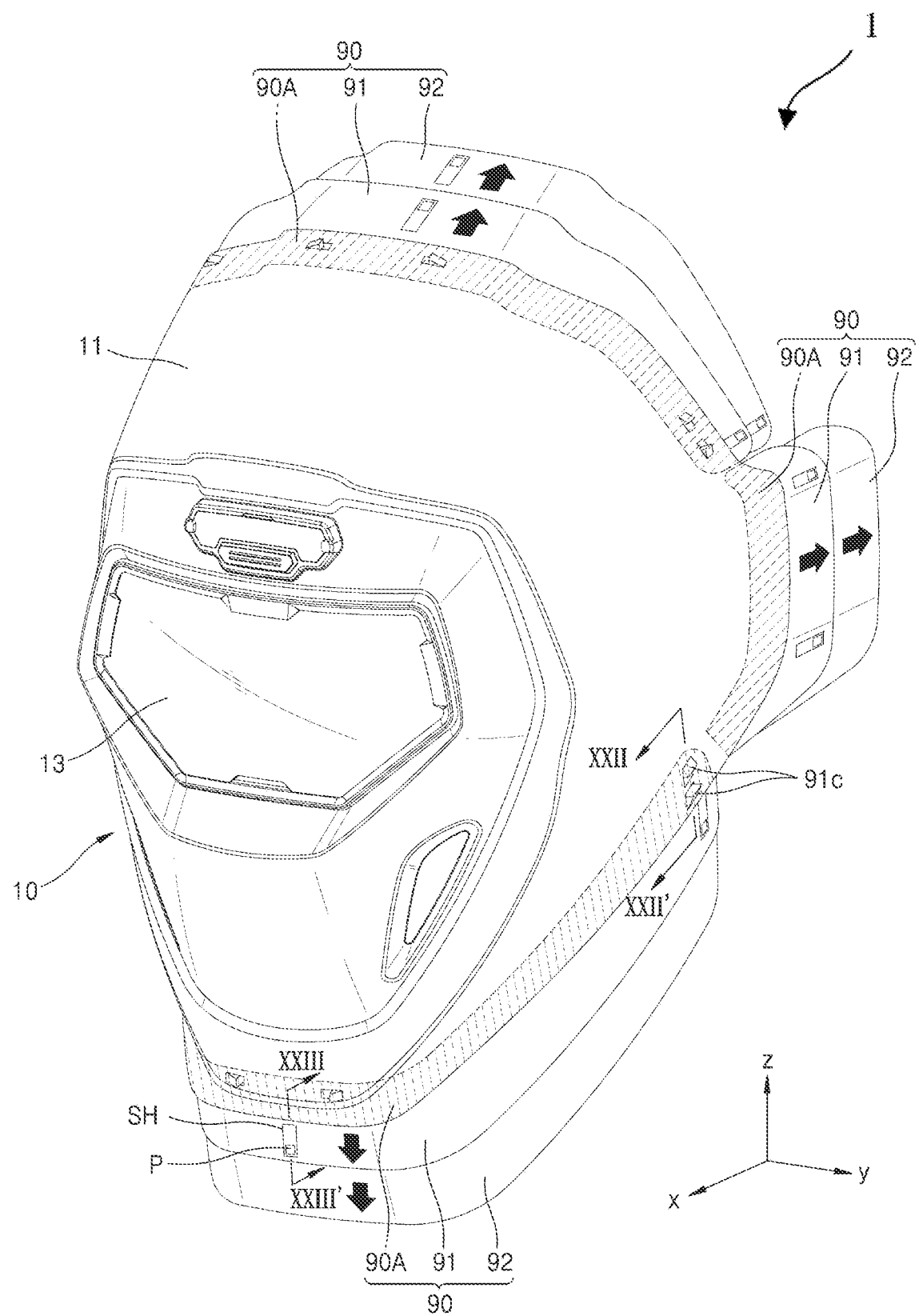
FIG. 21 is a perspective view of a welding protector according to an embodiment of the present disclosure.
Figure 22A:
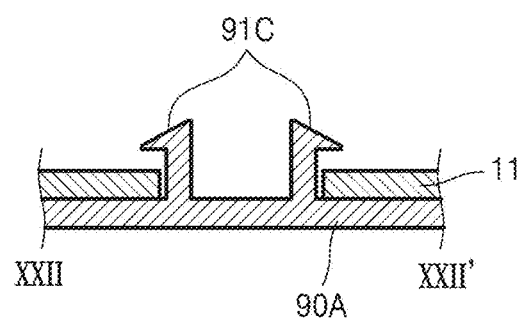
FIG. 22A is a cross-sectional view taken along line XXII-XXII' of FIG. 21 and illustrates coupling of a first portion of an auxiliary shield and a face shield according to an embodiment of the present disclosure.
Figure 22B:
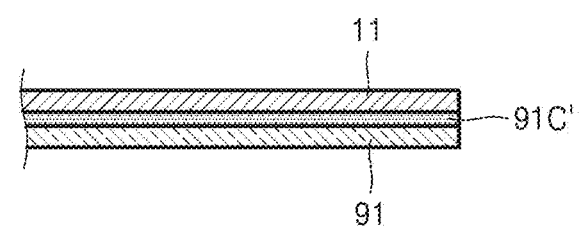
FIG. 22B is a cross-sectional view showing coupling of a first portion of an auxiliary shield and a face shield according to still an embodiment of the present disclosure.
Figure 23:
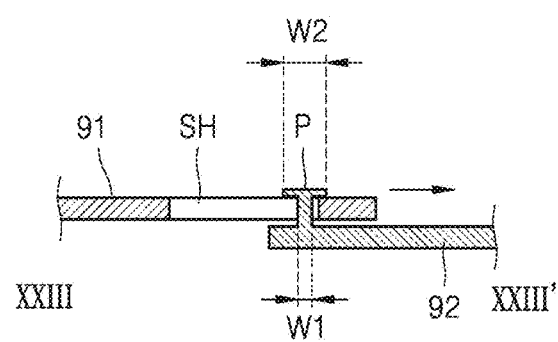
FIG. 23 is a cross-sectional view taken along line XXIII-XXIII' of FIG. 21 and illustrates movements of a first portion and a second portion of an auxiliary shield according to an embodiment of the present disclosure.

FIG. 21 is a perspective view of a welding protector according to an embodiment of the present disclosure. FIG. 22A is a cross-sectional view taken along line XXII-XXII' of FIG. 21, showing coupling of a first portion of an auxiliary shield and a face shield according to an embodiment of the present disclosure. FIG. 22B is a cross-sectional view showing coupling of a first portion of an auxiliary shield and a face shield according to still an embodiment of the present disclosure, and FIG. 23 is a cross-sectional view taken along line XXIII-XXIII' of FIG. 21 and illustrates movements of a first portion and a second portion of an auxiliary shield according to an embodiment of the present disclosure.

Referring to FIG. 21, each of the auxiliary shields 90 is positioned adjacent to one edge of a face shield 10 and may protect a portion of the body of the welder, for example, the top of the head part, the ears, and/or the neck. Since all of the auxiliary shields 90 have substantially the same structure, the auxiliary shield 90 protecting the neck of the welder will be mainly described.

The auxiliary shield 90 includes a plurality of portions, and an end portion 90A adjacent to a main body 11 may overlap a portion of the main body 11 of the face shield 10. The auxiliary shield 90 may be coupled to the main body 11 through a coupling member provided in the end portion 90A. The end portion 90A may be a partial region of a first portion 91 which will be described later.

For example, the end portion 90A may include a protrusion 91C having a hook shape as illustrated in FIG. 22A, and the protrusion 91C having a hook shape may be inserted into and coupled to a hook hole provided in the main body 11.

Alternatively, an end portion 90A may include a coupling layer 91C' as illustrated in FIG. 22B. The coupling layer 91C' may be a layer including an adhesive material and/or a Velcro layer.

The auxiliary shield 90 may include a first portion 91 and a second portion 92. The first portion 91 and the second portion 92 may linearly move in a sliding manner with respect to each other, and thus, the area of the auxiliary shield 90 may increase. The width of the auxiliary shield 90, for example, the maximum width may be selected in a range from about 1 cm to about 10 cm.

Referring to FIG. 23, the first portion 91 may include a slide hole SH, and the second portion 92 may include a protrusion P having a central portion inserted into the slide hole SH. The cross-section of the protrusion P may approximately have a T-shape in which a first width W1 of the central portion is less than a second width W2 of an upper portion. The protrusion P having the structure described above may be prevented from being separated or removed from the slide hole SH. The second portion 92 may linearly move relative to the first portion 91 as the protrusion P coupled to the slide hole SH moves in a longitudinal direction of the slide hole SH. The overlapping area of the first portion 91 and the second portion 92 may be reduced relatively, and the auxiliary shield 90 may increase in protection area. Similarly, one of the second portion 92 and a third portion 93 may include a protrusion, and the other may include a slide hole. Thus, the third portion 93 may linearly slide with respect to the second portion 92.

Figure 24:
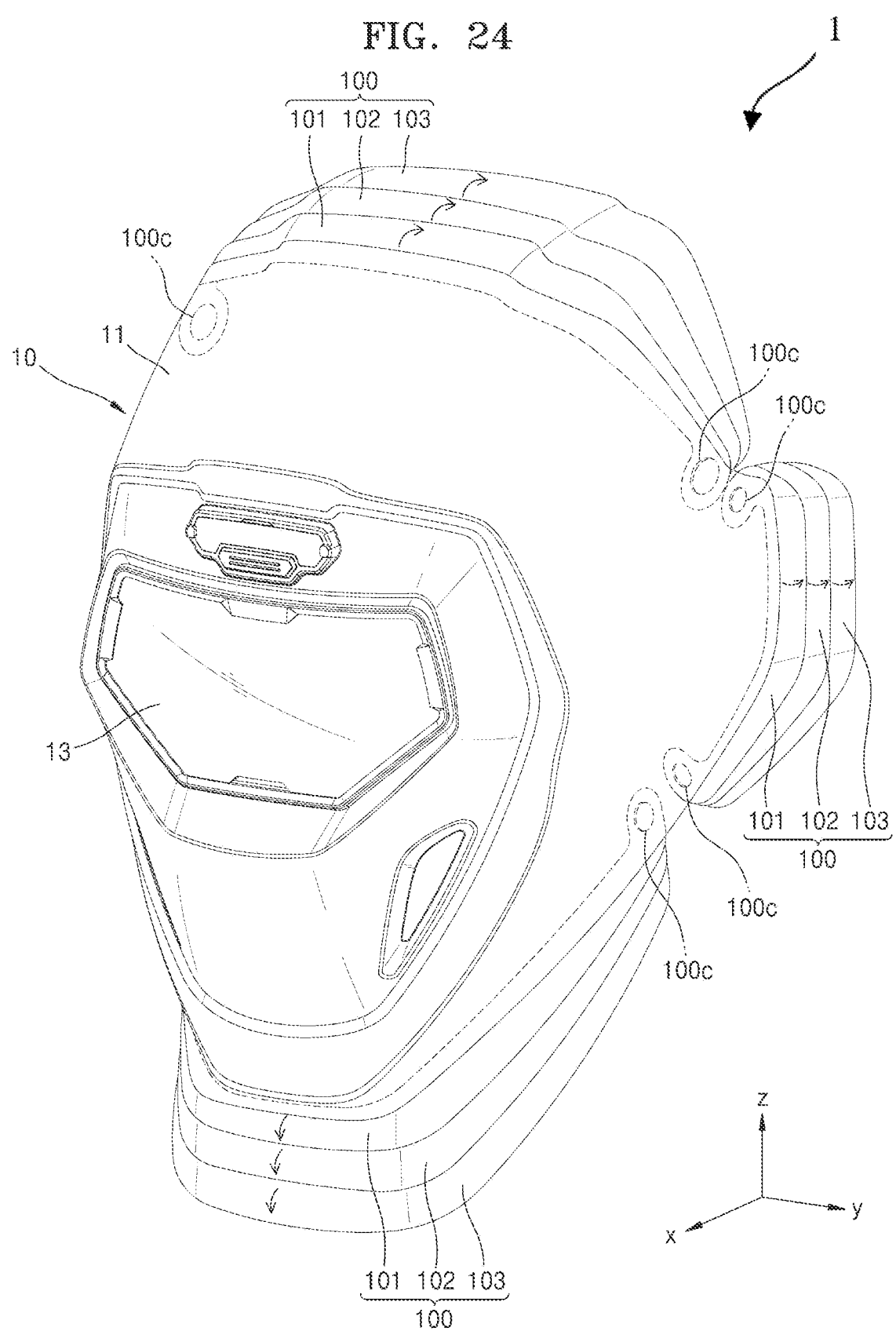
FIG. 24 is a perspective view of a welding protector according to an embodiment of the present disclosure.

FIG. 24 is a perspective view of a welding protector according to an embodiment of the present disclosure.

Referring to FIG. 24, the auxiliary shields 100 are positioned adjacent to one edge of a face shield 10 and may protect a portion of the body of the welder, for example, the top of the head part, the ears, and/or the neck. Because all of the auxiliary shields 100 have substantially the same structure, an auxiliary shield 100 that protects the top of the head part of the welder will be mainly described.

The auxiliary shield 100 may be fixed and coupled to the face shield 10 through coupling portions 100c positioned at both ends. The coupling portions 100c have an insertion structure of a hole and protrusion. One of the auxiliary shield 100 and a main body 11 may include a hole, and the other may include a protrusion inserted into the hole.

The auxiliary shield 100 may include a plurality of portions, for example, a first portion 101, a second portion 102, and a third portion 103, which are positioned adjacent to each other. In a first mode, the first portion 101 and the second portion 102 may overlap each other, and the second portion 102 and the third portion 103 may overlap each other. The first portion 101 and the third portion 103 may also overlap each other.

Subsequently, in a second mode, each portion of the auxiliary shield 100 may rotate around an axis. For example, the second portion 102 rotates around an axis passing through two coupling portions 100c, and thus, the overlapping area with the first portion 101 may be reduced. The third portion 103 rotates around the axis passing through two coupling portions 100c, and thus, the overlapping area with the second portion 102 may be reduced. The width of the auxiliary shield 100, for example, the maximum width may be selected in a range from about 1 cm to about 10 cm.

The embodiments of the present disclosure may provide the protector including the auxiliary shield which is easily adjustable in length depending on the body of the welder, and has excellent convenience of operation and use, enhanced storability and portability, and the like.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A welding protector comprising:
  a face shield configured to protect a face of a welder, wherein the face shield defines an interior volume; and
  an auxiliary shield disposed adjacent to one edge of the face shield,
  wherein:
    the auxiliary shield comprises a plurality of portions which overlap each other in a first mode and move to reduce an overlapping area when switching from the first mode to a second mode; and
    in the first mode, the plurality of portions are positioned in the interior volume of the face shield;
    a fixing member coupled to the face shield;
    wherein, in the first mode, fixing member couples the plurality of portions in the interior volume of the face shield; and
    wherein the fixing member is hingedly coupled to the face shield such that, from the second mode to the first mode, the fixing member is configured to rotate to couple the plurality of portions in the interior volume of the face shield.

2. The welding protector of claim 1, wherein the plurality of portions of the auxiliary shield are positioned on an inner surface of the face shield in the first mode.

3. The welding protector of claim 1, wherein the plurality of portions comprise a first portion and a second portion adjacent to each other, wherein the second portion linearly moves to reduce an overlapping area with the first portion when switching from the first mode to the second mode.

4. The welding protector of claim 1, wherein the plurality of portions comprise a first portion and a second portion adjacent to each other, wherein the second portion rotates around an axis when switching from the first mode to the second mode.

5. The welding protector of claim 1, wherein the plurality of portions comprise a first portion and a second portion adjacent to each other, wherein the first portion and the second portion are integrally coupled to each other, and the first portion and the second portion are foldable along a folding line between the first portion and the second portion.

6. The welding protector of claim 1, wherein the plurality of portions comprise a first portion and a second portion adjacent to each other, wherein the second portion linearly moves on the first portion when switching from the first mode to the second mode.

7. The welding protector of claim 1, wherein:
  the plurality of portions includes a first end and a second end;
  the first end is coupled to the face shield; and
  in the first mode, the fixing member covers the second end such that the fixing member retains the plurality of portions in the first mode.

8. The welding protector claim 7, wherein, in the first mode, the fixing member includes a surface shielding the plurality of portions.

9. A welding protector comprising:
  a face shield configured to protect a face of a welder, wherein the face shield defines an interior volume; and
  an auxiliary shield configured to cover a portion of a head part of the welder and positioned in the interior volume of the face shield,
  wherein the auxiliary shield comprises a hard material, and
    the auxiliary shield is movable in a direction away from the face shield to increase a covering area of the auxiliary shield configured to cover the portion of the head part;
    a fixing member coupled to the face shield;
    wherein, in the first mode, fixing member couples the plurality of portions in the interior volume of the face shield; and
  wherein the fixing member is hingedly coupled to the face shield such that, from the second mode to the first mode, the fixing member is configured to rotate to couple the plurality of portions in the interior volume of the face shield.

10. The welding protector of claim 9, wherein the auxiliary shield comprises a first portion and a second portion adjacent to each other, wherein the second portion is movable to reduce or increase an overlapping area with the first portion.

11. The welding protector of claim 10, wherein the second portion is linearly movable with respect to the first portion.

12. The welding protector of claim 11, wherein one of the first portion and the second portion comprises a slide hole that extends in the direction away from the face shield, and the other one comprises a protrusion having a central portion disposed in the slide hole.

13. The welding protector of claim 10, wherein the second portion is rotatable around an axis with respect to the first portion.

14. The welding protector of claim 13, wherein the auxiliary shield comprises a pair of coupling portions which are coupled to the face shield, and
  the second portion rotates with respect to the first portion around an axis that passes though the pair of coupling portions.

15. The welding protector of claim 10, wherein the first portion and the second portion linearly move in one direction with respect to the face shield, and after the linear movement, the second portion is rotatable to reduce or increase an overlapping area with the first portion.

16. A welding protector comprising:
  a face shield configured to protect a face of a welder, wherein the face shield defines an interior volume; and
  an auxiliary shield disposed adjacent to one edge of the face shield, wherein:
the auxiliary shield comprises a plurality of portions which overlap each other in a first mode and move to reduce an overlapping area when switching from the first mode to a second mode;
in the first mode, the plurality of portions are positioned in the interior volume of the face shield;
a fixing member coupled to the face shield;
wherein, in the first mode, fixing member couples the plurality of portions in the interior volume of the face shield;
wherein:
the fixing member includes a flexible strip; and
the flexible strip wraps around the plurality of portions to couple the plurality of portions in the interior volume of the face shield.

17. The welding protector of claim 16, wherein:
the face shield includes a securing point on an inner surface of the face shield; and
in the first mode, the flexible strip couples with the securing point to couple the plurality of portions in the interior volume of the face shield.

18. The welding protector of claim 17, wherein, in the first mode, the flexible strip couples with the securing point through one of a hook and loop fastener material, or a snap button feature.

\* \* \* \* \*